(12) United States Patent
Jiang et al.

(10) Patent No.: US 11,177,508 B2
(45) Date of Patent: Nov. 16, 2021

(54) LITHIUM-ION BATTERY AND APPARATUS

(71) Applicant: Contemporary Amperex Technology Co., Limited, Fujian (CN)

(72) Inventors: Yao Jiang, Ningde (CN); Chunhua Hu, Ningde (CN); Tiancheng Yi, Ningde (CN); Shushi Dou, Ningde (CN); Chengdu Liang, Ningde (CN)

(73) Assignee: Contemporary Amperex Technology Co., Limited, Ningde (CN)

( * ) Notice: Subject to any disclaimer, the term of this patent is extended or adjusted under 35 U.S.C. 154(b) by 0 days.

(21) Appl. No.: 17/146,758

(22) Filed: Jan. 12, 2021

(65) Prior Publication Data

US 2021/0143477 A1 May 13, 2021

Related U.S. Application Data

(63) Continuation of application No. PCT/CN2019/125319, filed on Dec. 13, 2019.

(30) Foreign Application Priority Data

Dec. 14, 2018 (CN) .......................... 201811537014.1

(51) Int. Cl.
| | |
|---|---|
| H01M 10/0567 | (2010.01) |
| H01M 4/36 | (2006.01) |
| H01M 4/505 | (2010.01) |
| H01M 4/525 | (2010.01) |
| H01M 10/0525 | (2010.01) |
| C07D 239/04 | (2006.01) |
| C07D 241/04 | (2006.01) |
| C07D 251/04 | (2006.01) |
| H01M 4/02 | (2006.01) |

(52) U.S. Cl.
CPC ....... *H01M 10/0567* (2013.01); *H01M 4/364* (2013.01); *H01M 4/505* (2013.01); *H01M 4/525* (2013.01); *H01M 10/0525* (2013.01); *C07D 239/04* (2013.01); *C07D 241/04* (2013.01); *C07D 251/04* (2013.01); *H01M 2004/028* (2013.01); *H01M 2220/20* (2013.01); *H01M 2300/0025* (2013.01)

(58) Field of Classification Search
None
See application file for complete search history.

(56) References Cited

U.S. PATENT DOCUMENTS

| | | |
|---|---|---|
| 2004/0142240 A1 | 7/2004 | Nagayama et al. |
| 2015/0064578 A1 | 3/2015 | Kang et al. |
| 2017/0069934 A1 | 3/2017 | Kim et al. |

FOREIGN PATENT DOCUMENTS

| | | |
|---|---|---|
| CN | 103022556 A | 4/2013 |
| CN | 103618081 A | 3/2014 |
| CN | 103078140 B | 4/2015 |
| CN | 105633460 A | 6/2016 |
| CN | 105655639 A | 6/2016 |
| CN | 106356561 A | 1/2017 |
| CN | 107431197 A | 12/2017 |
| CN | 105470473 B | 12/2018 |
| CN | 109148950 A | 1/2019 |
| CN | 110391460 A | 10/2019 |
| JP | H11-111332 A | 4/1999 |
| JP | 2001-357877 | * 12/2001 |
| JP | 2012-104439 A | 5/2012 |

OTHER PUBLICATIONS

Chinese Office Action dated Mar. 22, 2021, in connection with corresponding CN Application No. 201811537014.1 (16 pp., including machine-generated English translation).
Search Report dated Feb. 6, 2020 in corresponding International Application No. PCT/CN2019/125319; 6 pages.
Written Opinion dated Feb. 6, 2020 in corresponding International Application No. PCT/CN2019/125319; 13 pages.
Extended European Search Report dated Sep. 6, 2021, including Supplementary Search Report and the European Search Opinion, in connection with corresponding EP Application No. 19896283.9 (11pp.).

* cited by examiner

*Primary Examiner* — Laura Weiner
(74) *Attorney, Agent, or Firm* — Maier & Maier, PLLC

(57) ABSTRACT

The present application provides a lithium-ion battery and an apparatus, the lithium-ion battery includes an electrode assembly and an electrolyte, the electrode assembly includes a positive electrode sheet, a negative electrode sheet and a separator. A positive active material of the positive electrode sheet includes both $Li_{x1}Co_{y1}M1_{1-y1}O_{2-a}Q1_a$ and $Li_tNi_{m1}Co_{n1}M2_pM3_qO_{2-b}Q2_b$, a mass ratio of $Li_{x1}Co_{y1}M1_{1-y1}O_{2-a}Q1_a$ and $Li_tNi_{m1}Co_{n1}M2_pM3_qO_{2-b}Q2_b$ is 1:1-9:1. The electrolyte contains an additive A, the additive A is a six-membered nitrogen heterocyclic compound with multiple nitrile groups and with low oxidation potential. The lithium-ion battery according to the present application has excellent cycle performance and storage performance, especially under high temperature and high voltage conditions.

10 Claims, 3 Drawing Sheets

LITHIUM-ION BATTERY AND APPARATUS

CROSS-REFERENCE TO RELATED APPLICATIONS

This application is a continuation of International Application No. PCT/CN2019/125319, filed on Dec. 13, 2019, which claims priority to Chinese Patent Application No. 201811537014.1, filed on Dec. 14, 2018, both of which are hereby incorporated by reference in their entireties.

TECHNICAL FIELD

The present application relates to the field of energy storage materials, and more particularly, to a lithium-ion battery and an apparatus.

BACKGROUND

Lithium-ion batteries are widely used in electric vehicles and consumer electronics, due to their advantages of high energy density, high output power, long cycle life, and low environmental pollution. The current demands for lithium-ion batteries are: high voltage, high power, long cycle life, long storage life, and excellent safety performance.

Lithium-ion batteries currently widely use $LiCoO_2$ as a positive active material, and they have a relatively stable performance when cycled between fully discharged $LiCoO_2$ and semi-charged $Li_{0.5}CoO_2$ (4.2V vs. Li), and thus, in fact, lithium ions actually used are only ½ of its actual lithium ion content. When the voltage is greater than 4.2V, the remaining ½ content of lithium ions of in $LiCoO_2$ can continue to be extracted, but in a process of deep delithiation, $Co^{3+}$ will be oxidized to very unstable $Co^{4+}$, which will oxidize the electrolyte together with surface oxygen that has lost a large number of electrons. In this case, a large amount of gas will be generated inside the batteries, causing the batteries to swell. At the same time, due to a corrosive effect of HF in the electrolyte on a surface of a positive electrode, $Co^{4+}$ is dissolved in the electrolyte and then deposited on a surface of a negative electrode, which catalyzes reduction of the electrolyte, and also generates a large amount of gas and causes the batteries to swell. Additionally, due to a large overlap between 3d energy level of Co and 2p energy level of O, deep delithiation will also cause lattice oxygen to lose a large number of electrons, so that $LiCoO_2$ unit cells shrink sharply in a c-axis direction, inducing local bulk phase structure to be unstable or even collapse, and finally resulting in loss of active sites of $LiCoO_2$ and rapid decrease of the lithium-ion battery capacity. Therefore, the performance of $LiCoO_2$ is very poor when used in a system with a high voltage greater than 4.2V.

In view of the above, the present application is hereby proposed.

SUMMARY

In view of the problems existing in the background technology, an object of the present application is to provide a lithium-ion battery and an apparatus, the lithium-ion battery has excellent cycle performance and storage performance, especially under high temperature and high voltage conditions.

In order to achieve the above object, in a first aspect, the present application provides a lithium-ion battery, which includes an electrode assembly and an electrolyte, the electrode assembly includes a positive electrode sheet, a negative electrode sheet, and a separator. A positive active material of the positive electrode sheet includes both $Li_{x1}Co_{y1}M1_{1-y1}O_{2-a}Q1_a$ and $Li_iNi_{m1}Co_{n1}M2_pM3_qO_{2-b}Q2_b$, a mass ratio of $Li_{x1}Co_{1-y1}M1_{1-y1}O_{2-a}Q1_a$ and $Li_iNi_{m1}Co_{n1}M2_pM3_qO_{2-b}Q2_b$ is 1:1-9:1; where $0.5 \leq x1 \leq 1.2$, $0.8 \leq y1 \leq 1.0$, $0 \leq a \leq 0.1$, M1 is selected from one or more of Al, Ti, Zr, Y, and Mg, and Q1 is selected from one or more of F, Cl, and S; $0.5 \leq 1 \leq 1.2$, $0.33 \leq m1 \leq 0.85$, $0.1 \leq n1 \leq 0.33$, $0.1 \leq p \leq 0.33$, $0 \leq q \leq 0.1$, and $m1+n1+p+q=1$, $0 \leq b \leq 0.1$, M2 is selected from one or two of Mn and Al, M3 is selected from one or more of Zr, Zn, Cu, Cr, Mg, Fe, V, Ti, Y, and Nb, Q2 is selected from one or more of F, Cl, and S. The electrolyte contains an additive A, the additive A is selected from one or more of compounds represented by Formula I-1, Formula I-2, and Formula I-3. In the Formula I-1, Formula I-2 and Formula I-3: $R_1$, $R_2$, $R_3$ and $R_4$ each are independently selected from a hydrogen atom, a halogen atom, a substituted or unsubstituted $C_1$-$C_{12}$ alkyl group, a substituted or unsubstituted $C_1$-$C_{12}$ alkoxyl group, a substituted or unsubstituted amido group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, and a substituted or unsubstituted $C_2$-$C_{12}$ heterocyclyl group, where a substituent is selected from one or more of a halogen atom, a nitrile group, a $C_1$-$C_6$ alkyl group, a $C_2$-$C_6$ alkenyl group, and a $C_1$-$C_6$ alkoxyl group; x, y and z each are independently selected from an integer of 0-8; m, n and k each are independently selected from an integer of 0-2.

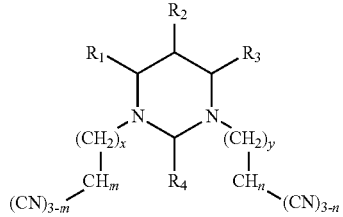

Formula I-1

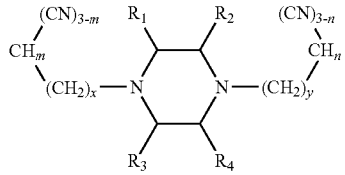

Formula I-2

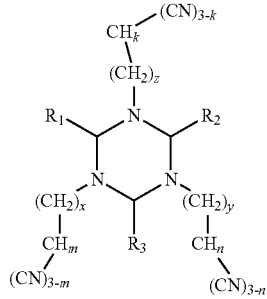

Formula I-3

In a second aspect of the present application, the present application discloses an apparatus, which includes the lithium-ion battery according to the first aspect of the present application.

Compared with the prior art, the present application includes at least the following beneficial effects:

the present application uses a positive active material including a metal ion M-doped lithium cobalt oxide material $Li_{x1}Co_{y1}M1_{1-y1}O_{2-a}Q1_a$, where doping element M serves as a skeleton in the lithium cobalt oxide material, and can reduce lattice deformation amount in the process of deep delithiation of the lithium cobalt oxide material, delay the degradation of a bulk phase structure of the lithium cobalt oxide material, and improve the structural stability of a lithium-ion battery when used at high voltage greater than 4.2V.

In the present application, a certain amount of a ternary material $Li_{x1}Ni_{m1}Co_{n1}M2_pM3_qO_{2-b}Q2_b$ is also mixed in the lithium cobalt oxide material $Li_{x1}Co_{y1}M1_{1-y1}O_{2-a}Q1_a$, the ternary material can be evenly distributed in gaps between particles of the lithium cobalt oxide material, so as to separate the lithium cobalt oxide material effectively, and at the same time, after mixing, compaction density of the positive electrode sheet can also be increased, and energy density of the lithium-ion battery can be increased; furthermore, relatively high thermal stability of the ternary material can not only ensure its own structural stability, but also can effectively prevent heat transmission caused by the decomposition of local lithium cobalt oxide material, improving thermal stability of the entire positive electrode sheet.

The electrolyte used in the present application further contains a six-membered nitrogen heterocyclic compound with multiple nitrile groups and with a low oxidation potential, and then during battery formation, a stable complex layer can be formed on a surface of the positive active material, which can effectively passivate the surface of the positive active material, reduce activity of the surface of the positive active material, and inhibit the transition metal (especially cobalt) from being dissolved into the electrolyte, thereby reducing gas production in the battery while reducing side reactions.

Therefore, the lithium-ion battery according to the present application has excellent cycle performance and storage performance, especially under high temperature and high voltage conditions. The apparatus according to the present application includes the lithium-ion battery according to the first aspect of the present application, and thus has at least the same advantages as the lithium-ion battery.

DETAILED DESCRIPTION OF EMBODIMENTS

Figure 1:
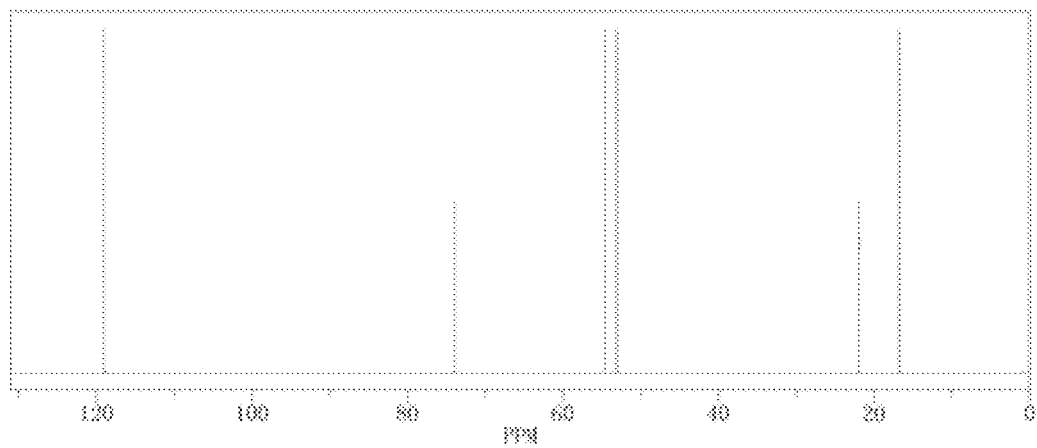
FIG. 1 is a carbon nuclear magnetic resonance spectrum of a compound A1.

A lithium-ion battery and an apparatus according to the present application will be described in detail below.

Firstly, the lithium-ion battery according to a first aspect of the present application is described.

The lithium-ion battery according to the present application includes an electrode assembly and an electrolyte, the electrode assembly includes a positive electrode sheet, a negative electrode sheet, and a separator.

In the lithium-ion battery according to the present application, a positive active material of the positive electrode sheet includes both $Li_{x1}Co_{y1}M1_{1-y1}O_{2-a}Q1_a$ and $Li_iNi_{m1}Co_{n1}M2_pM3_qO_{2-b}Q2_b$, a mass ratio of $Li_{x1}Co_{y1}M1_{1-y1}O_{2-a}Q1_a$ and $Li_iNi_{m1}Co_{n1}M2_pM3_qO_{2-b}Q2_b$ is 1:1-9:1, where $0.5 \leq x1 \leq 1.2$, $0.8 \leq y1 < 1.0$, $0 \leq a \leq 0.1$, M1 is selected from one or more of Al, Ti, Zr, Y, and Mg, and Q1 is selected from one or more of F, Cl, and S; $0.5 \leq 1 \leq 1.2$, $0.33 \leq m1 \leq 0.85$, $0.1 \leq n1 \leq 0.33$, $0.1 \leq p \leq 0.33$, $0.1 \leq q \leq 0.1$, and $m1+n1+p+q=1$, $0 \leq b \leq 0.1$, M2 is selected from one or two of Mn and Al, M3 is selected from one or more of Zr, Zn, Cu, Cr, Mg, Fe, V, Ti, Y, and Nb, and Q2 is selected from one or more of F, Cl, and S.

In the lithium-ion battery according to the present application, the electrolyte contains an additive A, the additive A is selected from one or more of compounds represented by Formula I-1, Formula I-2, and Formula I-3. In the Formula I-1, Formula I-2 and Formula I-3: $R_1$, $R_2$, $R_3$ and $R_4$ each are independently selected from a hydrogen atom, a halogen atom, a substituted or unsubstituted $C_1$-$C_{12}$ alkyl group, a substituted or unsubstituted $C_1$-$C_{12}$ alkoxyl group, a substituted or unsubstituted $C_1$-$C_{12}$ amido group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, and a substituted or unsubstituted $C_2$-$C_{12}$ heterocyclyl group, where a substituent (refer to a substituted situation of the "substituted or unsubstituted" in the present application) is selected from one or more of a halogen atom, a nitrile group, a $C_1$-$C_6$ alkyl group, a $C_2$-$C_6$ alkenyl group, and a $C_1$-$C_6$ alkoxyl group; x, y and z each are independently selected from an integer of 0-8; and m, n and k each are independently selected from an integer of 0-2.

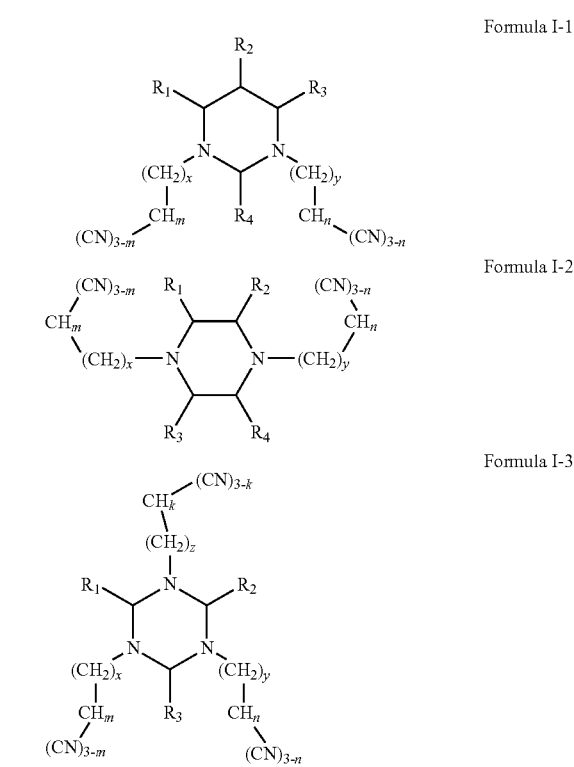

Formula I-1

Formula I-2

Formula I-3

The lithium-ion battery according to the present application has excellent cycle performance and storage performance, especially under high temperature and high voltage conditions.

Specifically:

(1) The present application uses a positive active material including a metal ion M-doped lithium cobalt oxide material $Li_{x1}Co_{y1}M_{1-y1}O_{2-z1}Q_{z1}$, where doping element M serves as a skeleton in the lithium cobalt oxide material, and can reduce lattice deformation amount in the process of deep delithiation of the lithium cobalt oxide material, delay the degradation of a bulk phase structure of the lithium cobalt oxide material, and improve the structural stability of a lithium-ion battery when used at high voltage greater than 4.2V.

(2) The positive active material according to the present application includes both the lithium cobalt oxide material $Li_{x1}Co_{y1}M1_{1-y1}O_{2-a}Q1_a$ and the ternary material $Li_lNi_{m1}Co_{n1}M2_pM3_qO_{2-b}Q2_b$. Generally, under the same cut-off voltage, thermal stability of the ternary material is better than that of the lithium cobalt oxide material, gram volume of the ternary material is higher than that of the lithium cobalt oxide material, and particle size of the ternary material is smaller than that of the lithium cobalt oxide material. Therefore, by mixing the lithium cobalt oxide material $Li_{x1}Co_{y1}M1_{1-y1}O_{2-a}Q1_a$ with a certain amount of the ternary material $Li_lNi_{m1}Co_{n1}M2_pM3_qO_{2-b}Q2_b$, the ternary material can be evenly distributed in gaps between particles of the lithium cobalt oxide material, so as to separate the lithium cobalt oxide material effectively, and meanwhile, after mixing, the compaction density of the positive electrode sheet can also be increased, and the energy density of the lithium-ion battery can be increased. Furthermore, when the lithium-ion battery is used at a high temperature, high thermal stability of the ternary material can not only ensure its own structural stability, but also can effectively prevent the heat transmission caused by the decomposition of local lithium cobalt oxide material, improving the thermal stability of the entire positive electrode sheet. In the mixed positive active material, when the content of the ternary material is too low, it cannot effectively separate the lithium cobalt oxide material, cannot provide good protection, and cannot improve the thermal stability of the entire positive electrode sheet; when the content of the ternary material is too high, the compaction density of the positive electrode sheet is not high, and the energy density of the lithium-ion battery is not good. Therefore, an optimal mixing ratio is $Li_{x1}Co_{y1}M1_{1-y1}O_{2-a}Q1_a$:$Li_lNi_{m1}Co_{n1}M2_pM3_qO_{2-b}Q2_b$=1:1-9:1.

(3) The additive A contained in the electrolyte according to the present application is a six-membered nitrogen heterocyclic compound with multiple nitrile groups and with low oxidation potential, the nitrogen atoms in the nitrile groups include a lone pair of electrons, which has strong complexation with the transition metal in the positive active material, and after the additive A is applied into the electrolyte, during formation of the battery, it can be adsorbed on a surface of the positive active material to produce a loose and porous complex layer, and effectively passivate the surface of the positive active material. The complex layer can isolate a direct contact between the surface of the positive active material and the electrolyte, and reduce activity of the surface of the positive active material, and can also reduce a large number of side reactions on the surface of the positive active material and inhibit the transition metal (especially cobalt) from being dissolved into the electrolyte, so that the electrolyte according to the present application can reduce side reaction products and lower gas production.

(4) The additive A according to the present application has a special six-membered nitrogen heterocyclic structure, a distance between nitrile groups is closer to a distance between transition metals on the surface of the positive active material, which can maximize the complexation of nitrile groups, and make maximum quantity of nitrile groups perform the complexation; therefore, compared with a conventional linear nitrile compound, the six-membered nitrogen heterocyclic compound with multiple nitrile groups according to the present application has a better passivation effect.

(5) The special six-membered nitrogen heterocyclic structure of the additive A according to the present application can also lower the oxidation potential of the molecule, and thus form a stable complex layer on the surface of the positive active material during formation of the battery, improving the electrochemical performance of the entire battery system, such as reducing gas production and increasing cycle life under high temperature and high voltage.

In the lithium-ion battery according to the present application, preferably, based on total mass of the electrolyte, a mass percentage content of the additive A is 0.1%40%. If the content of the additive A is too low, the improvement effect of the additive A on the electrolyte will not be obvious; if the content of the additive A is too high, the complex layer formed by it adsorbed on the surface of the positive active material is too thick and dense, which affects the diffusion and migration of lithium ions, and enables the impedance of the positive electrode to be greatly increased, and at the same time, too high content of the additive A also leads to an increase of overall viscosity of the electrolyte and a decrease of ion conductivity, and therefore, too high content will affect performance playing of the lithium-ion battery. Preferably, an upper limit of content range of the additive A can be optionally selected from 10%, 9%, 8%, 7%, 6%, 5%, 4.5%, 4%, 3.5%, 3%, 2.5%, 2%, 1.5%, 1%, and 0.8%, and a lower limit of the content range of the additive A can be optionally selected from 0.1%, 0.2%, 0.3%, 0.4%, 0.5%, 0.6%, 0.7%, 0.8%, 0.9%, 1.0%, and 1.2%.

Further preferably, based on the total mass of the electrolyte, the mass percentage content of the additive A is 0.1%-6%. Further more preferably, based on the total mass of the electrolyte, the mass percentage content of the additive A is 0.1%-3.5%.

In an embodiment of the lithium-ion battery according to the present application, the electrolyte can further contain an additive B, and the additive B is $LiBF_4$. In a high-voltage lithium-ion battery system, the positive active material is easy to release oxygen, and B atom in $LiBF_4$ can stabilize oxygen atom in the positive active material, and play a role in inhibiting oxygen release of the positive active material, thus facilitating to increase a life, especially storage life, of the high-voltage lithium-ion battery system.

Preferably, based on the total mass of the electrolyte, a mass percentage content of the additive B is 0.1%-10%. More preferably, based on the total mass of the electrolyte, the mass percentage content of the additive B is 0.1%-5%.

In another embodiment of the lithium-ion battery according to the present application, the electrolyte can further contain an additive C, the additive C is selected from one or more of vinylene carbonate (VC), fluoroethylene carbonate (FEC), and 1,3-propane sultone (PS). The additive C can form a surface film, which contains one or more of double bonds, fluorine atoms, and sulfonate groups, on a surface of the positive or negative electrode. The surface film has good chemical, electrochemical, mechanical and thermal stability, can smoothly conduct lithium ions and meanwhile isolate the direct contact between the electrolyte and surfaces of the positive and negative electrodes, playing a role of inhibiting oxidation and reduction side reactions of the surfaces of the positive and negative electrodes, and thus gas production of the battery can be significantly inhibited, and the cycle life and the storage life of the high-voltage lithium-ion battery system can be increased.

Preferably, based on the total mass of the electrolyte, a mass percentage content of the additive C is 0.1%-10%. More preferably, based on the total mass of the electrolyte, the mass percentage content of the additive C is 0.1%-5%.

In yet another embodiment of the lithium-ion battery according to the present application, the electrolyte can contain both the additive B and the additive C. Preferably, based on the total mass of the electrolyte, mass percentages of the additive B and the additive C are 0.1%-10%.

In the lithium-ion battery according to the present application, the electrolyte further includes an organic solvent and a lithium salt.

The organic solvent used in the electrolyte of the embodiments of the present application can include cyclic carbonate and chain carbonate, and it can further improve the cycle performance and storage performance of the lithium-ion battery under high temperature and high voltage conditions, and it is easy to adjust the conductivity of the electrolyte to a suitable range, which is more conducive to enabling each additive to achieve better film-forming effect.

The organic solvent used in the electrolyte of the embodiments of the present application can also include carboxylate, that is, the organic solvent according to the present application can include a mixture of cyclic carbonate, chain carbonate, and carboxylate. The carboxylate has characteristics of large dielectric constant and low viscosity, which can effectively prevent the association of lithium ions and anions in the electrolyte, and meanwhile it is more advantageous than cyclic carbonate and chain carbonate in terms of ion conduction, especially it can ensure that the electrolyte has good ion conduction characteristics at a low temperature.

Where based on a total mass of the organic solvent, a mass percentage content of the cyclic carbonate can be 15%-55% preferably 25%-50%; a mass percentage content of the chain carbonate can be 15%-74%, preferably 25%-70%; and a mass percentage content of the carboxylate can be 0.1%-70%, preferably 5%-50%.

Specifically, the cyclic carbonate can be selected from one or more of ethylene carbonate, propylene carbonate, 1,2-butene carbonate, and 2,3-butanediol carbonate. More preferably, the cyclic carbonate can be selected from one or more of ethylene carbonate and propylene carbonate.

Specifically, the chain carbonate is an asymmetric chain carbonate which can be selected from one or more of ethyl methyl carbonate, methyl propyl carbonate, methyl isopropyl carbonate, methyl butyl carbonate, and ethyl propyl carbonate; the chain carbonate is a symmetric chain carbonate which can be selected from one or more of dimethyl carbonate, diethyl carbonate, dipropyl carbonate, and dibutyl carbonate; and the chain carbonate can also be a mixture of the asymmetric chain carbonate and the symmetric chain carbonate as described above.

Specifically, the carboxylate can be selected from one or more of methyl pivalate, ethyl pivalate, propyl pivalate, butyl pivalate, methyl butyrate, ethyl butyrate, propyl butyrate, butyl butyrate, methyl propionate, ethyl propionate, propyl propionate, butyl propionate, methyl acetate, ethyl acetate, propyl acetate, and butyl acetate.

The lithium salt used in the electrolyte of the embodiments of the present application can be selected from one or more of $LiPF_6$, $LiPO_2F_2$, $Li_2PO_3F$, $LiSO_3F$, lithium trifluoro ((methylsulfonyl)oxy) borate, $LiN(SO_2F)_2$, $LiN(SO_2CF_3)_2$, $LiN(SO_2C_2F_5)_2$, bis[oxalate-O,O'] lithium borate, difluoro bis[oxalate-O,O'] lithium phosphate, tetrafluoro[oxalate-O, O'] lithium phosphate.

In the lithium-ion battery according to the present application, the concentration of the lithium salt is not particularly limited, and can be adjusted reasonably according to actual needs.

In the lithium-ion battery according to the present application, preferably, the conductivity of the electrolyte at 25° C. is 4 mS/cm-12 mS/cm.

In the lithium-ion battery according to the present application, a preparation method of the electrolyte is not limited, and the electrolyte can be prepared according to a conventional method.

In the lithium-ion battery according to the present application, $Li_{x1}Co_{y1}M1_{1-y1}O_{2-a}Q1_a$ can be specifically selected from one or more of $LiCo_{0.9}Zr_{0.1}O_2$, $LiCo_{0.9}Ti_{0.1}O_2$, $Li_{1.05}Co_{0.8}Mg_{0.2}O_2$, $Li_{1.01}Co_{0.98}Mg_{0.01}Ti_{0.005}Al_{0.005}O_2$, $Li_{1.05}Co_{0.98}Mg_{0.005}Zr_{0.005}Ti_{0.01}O_{1.9}F_{0.1}$, $Li_{1.1}Co_{0.95}Mg_{0.01}Zr_{0.01}Al_{0.03}O_2$, $Li_{1.04}Co_{0.95}Mg_{0.02}Zr_{0.03}O_{1.95}F_{0.05}$, $Li_{1.06}Co_{0.96}Mg_{0.02}Ti_{0.02}O_2$, $Li_{1.08}Co_{0.97}Mg_{0.01}Zr_{0.01}Al_{0.01}O_{1.9}S_{0.1}$, $Li_{1.09}Co_{0.98}Mg_{0.01}Ti_{0.005}Al_{0.005}O_2$, $Li_{1.085}Co_{0.98}Zr_{0.01}Ti_{0.005}Al_{0.005}O_{1.9}Cl_{0.1}$, $Li_{1.03}Co_{0.96}Mg_{0.01}Zr_{0.01}Ti_{0.01}Al_{0.01}O_2$, $Li_{1.04}Co_{0.97}Zr_{0.01}Al_{0.02}O_{1.9}F_{0.1}$, $Li_{1.07}Co_{0.97}Zr_{0.01}Ti_{0.01}Al_{0.01}O_{1.9}S_{0.1}$, $Li_{1.02}Co_{0.96}Mg_{0.02}Zr_{0.015}Ti_{0.005}O_{1.9}S_{0.1}$, $Li_{1.03}Co_{0.98}Ti_{0.01}Al_{0.01}O_{1.9}Cl_{0.1}$, $Li_{1.05}Co_{0.97}Mg_{0.01}Zr_{0.01}Al_{0.01}O_{1.9}Cl_{0.1}$, $Li_{1.04}Co_{0.95}Zr_{0.02}Ti_{0.03}O_{1.9}F_{0.1}$, $Li_{1.09}Co_{0.97}Mg_{0.02}Ti_{0.01}O_{1.95}F_{0.05}$, $Li_{1.03}Co_{0.95}Mg_{0.03}Ti_{0.02}O_{1.9}S_{0.1}$, and $Li_{1.04}Co_{0.97}Zr_{0.01}Ti_{0.01}Al_{0.01}O_{1.9}S_{0.1}$.

In the lithium-ion battery according to the present application, $Li_lNi_{m1}Co_{n1}M2_pM3_qO_{2-b}Q2_b$ can be specifically selected from one or more of $LiNi_{1/3}Co_{1/3}Mn_{1/3}O_2$, $LiNi_{0.5}Co_{0.2}Mn_{0.3}O_2$, $LiNi_{0.6}Co_{0.2}Mn_{0.2}O_2$, $LiNi_{0.8}Co_{0.1}Mn_{0.1}O_2$, $LiNi_{0.8}Co_{0.1}Al_{0.1}O_2$, $LiNi_{0.85}Co_{0.15}Al_{0.05}O_2$, $Li_{1.01}Ni_{0.33}Co_{0.33}Mn_{0.31}Mg_{0.01}Ti_{0.005}Al_{0.005}O_2$, $Li_{1.05}Ni_{0.33}Co_{0.33}Mn_{0.31}Mg_{0.005}Zr_{0.005}Ti_{0.01}O_{1.9}F_{0.1}$, $Li_{1.1}Ni_{0.33}Co_{0.31}Mn_{0.31}Mg_{0.01}Zr_{0.01}Al_{0.03}O_2$, $Li_{1.04}Ni_{0.33}Co_{0.31}Mn_{0.31}Mg_{0.02}Zr_{0.03}O_{1.95}F_{0.05}$, $Li_{1.06}Ni_{0.33}Co_{0.32}Mn_{0.31}Mg_{0.02}Ti_{0.02}O_2$, $Li_{1.08}Ni_{0.33}Co_{0.32}Mn_{0.31}Mg_{0.01}Zr_{0.01}Al_{0.01}O_{1.9}S_{0.1}$, $Li_{1.09}Ni_{0.33}Co_{0.33}Mn_{0.32}Mg_{0.01}Ti_{0.005}Al_{0.005}O_2$, $Li_{1.085}Ni_{0.33}Co_{0.33}Mn_{0.32}Zr_{0.01}Ti_{0.005}Al_{0.005}O_{1.9}Cl_{0.1}$, $Li_{1.03}Ni_{0.33}Co_{0.32}Mn_{0.31}Mg_{0.01}Zr_{0.01}Ti_{0.01}Al_{0.01}O_2$, $Li_{1.04}Ni_{0.33}Co_{0.32}Mn_{0.32}Zr_{0.01}Al_{0.02}O_{1.9}F_{0.1}$, $Li_{1.07}Ni_{0.33}Co_{0.32}Mn_{0.32}Zr_{0.01}Ti_{0.01}Al_{0.01}O_{1.9}S_{0.1}$, $Li_{1.02}Ni_{0.33}Co_{0.32}Mn_{0.31}Mg_{0.02}Zr_{0.015}Ti_{0.005}O_{1.9}S_{0.1}$, $Li_{1.03}Ni_{0.33}Co_{0.33}Mn_{0.32}Ti_{0.01}Al_{0.01}O_{1.9}Cl_{0.1}$, $Li_{1.05}Ni_{0.33}Co_{0.32}Mn_{0.32}Mg_{0.01}Zr_{0.01}Al_{0.01}O_{1.9}Cl_{0.1}$, $Li_{1.04}Ni_{0.33}Co_{0.31}Mn_{0.31}Zr_{0.02}Ti_{0.03}O_{1.9}F_{0.1}$, $Li_{1.09}Ni_{0.33}Co_{0.32}Mn_{0.32}Mg_{0.02}Ti_{0.01}O_{1.95}F_{0.05}$, $Li_{1.03}Ni_{0.33}Co_{0.31}Mn_{0.31}Mg_{0.03}Ti_{0.02}O_{1.9}S_{0.1}$, $Li_{1.04}Ni_{0.33}Co_{0.31}Mn_{0.31}Zr_{0.01}Ti_{0.01}Al_{0.01}O_{1.9}S_{0.1}$, $Li_{1.01}Ni_{0.50}Co_{0.20}Mn_{0.28}Mg_{0.01}Ti_{0.005}Al_{0.005}O_2$, $Li_{1.05}Ni_{0.50}Co_{0.20}Mn_{0.28}Mg_{0.005}Zr_{0.005}Ti_{0.01}O_{1.9}F_{0.1}$, $Li_{1.1}Ni_{0.50}Co_{0.20}Mn_{0.25}Mg_{0.01}Zr_{0.01}Al_{0.03}O_2$,
$Li_{1.04}Ni_{0.50}Co_{0.20}Mn_{0.25}Mg_{0.02}Zr_{0.03}O_{1.95}F_{0.05}$,
$Li_{1.06}Ni_{0.50}Co_{0.20}Mn_{0.26}Mg_{0.02}Ti_{0.02}O_2$,
$Li_{1.08}Ni_{0.50}Co_{0.20}Mn_{0.27}Mg_{0.01}Zr_{0.01}Al_{0.01}O_{1.9}S_{0.1}$,
$Li_{1.09}Ni_{0.60}Co_{0.20}Mn_{0.18}Mg_{0.01}Ti_{0.005}Al_{0.005}O_2$,
$Li_{1.085}Ni_{0.60}Co_{0.20}Mn_{0.18}Zr_{0.01}Ti_{0.005}Al_{0.005O1.9}Cl_{0.1}$,
$Li_{1.03}Ni_{0.60}Co_{0.20}Mn_{0.16}Mg_{0.01}Zr_{0.01}Ti_{0.01}Al_{0.01}O_2$,
$Li_{1.04}Ni_{0.60}Co_{0.20}Mn_{0.17}Zr_{0.01}Al_{0.02}O_{1.9}F_{0.1}$,
$Li_{1.07}Ni_{0.60}Co_{0.20}Mn_{0.17}Zr_{0.01}Ti_{0.01}Al_{0.01}O_{1.9}S_{0.1}$,
$Li_{1.02}Ni_{0.60}Co_{0.20}Mn_{0.16}Mg_{0.02}Zr_{0.015}Ti_{0.005O1.9}S_{0.1}$,
$Li_{1.03}Ni_{0.60}Co_{0.20}Mn_{0.18}Ti_{0.01}Al_{0.01}O_{1.9}Cl_{0.1}$,
$Li_{1.05}Ni_{0.60}Co_{0.20}Mn_{0.17}Mg_{0.01}Zr_{0.01}Al_{0.01}O_{1.9}Cl_{0.1}$,
$Li_{1.04}Ni_{0.60}Co_{0.20}Mn_{0.15}Zr_{0.02}Ti_{0.03}O_{1.9}F_{0.1}$,
$Li_{1.09}Ni_{0.60}Co_{0.20}Mn_{0.17}Mg_{0.02}Ti_{0.01}O_{1.95}F_{0.05}$,
$Li_{1.03}Ni_{0.60}Co_{0.20}Mn_{0.15}Mg_{0.03}Ti_{0.02}O_{1.9}S_{0.1}$,
$Li_{1.04}Ni_{0.60}Co_{0.20}Mn_{0.17}Zr_{0.01}Ti_{0.01}Al_{0.01}O_{1.9}S_{0.1}$,
$Li_{1.01}Ni_{0.60}Co_{0.20}Mn_{0.18}Mg_{0.01}Ti_{0.005}Al_{0.005}O_2$, $Li_{1.05}Ni_{0.60}Co_{0.20}Mn_{0.18}Mg_{0.005}Zr_{0.005}Ti_{0.01}O_{1.9}F_{0.1}$,
$Li_{1.10}Ni_{0.60}Co_{0.20}Mn_{0.15}Mg_{0.01}Zr_{0.01}Al_{0.03}O_2$,
$Li_{1.04}Ni_{0.60}Co_{0.20}Mn_{0.15}Mg_{0.02}Zr_{0.03}O_{1.95}F_{0.05}$,
$Li_{1.06}Ni_{0.60}Co_{0.20}Mn_{0.15}Mg_{0.02}Ti_{0.02}O_2$,
$Li_{1.08}Ni_{0.60}Co_{0.20}Mn_{0.17}Mg_{0.01}Zr_{0.01}Al_{0.01}O_{1.9}S_{0.1}$,
$Li_{1.09}Ni_{0.60}Co_{0.20}Mn_{0.18}Mg_{0.01}Ti_{0.005}Al_{0.005}O_2$,
$Li_{1.085}Ni_{0.60}Co_{0.20}Mn_{0.18}Zr_{0.01}Ti_{0.005}Al_{0.005}O_{1.9}Cl_{0.1}$,
$Li_{1.03}Ni_{0.60}Co_{0.2}Mn_{0.16}Mg_{0.01}Zr_{0.01}Ti_{0.01}Al_{0.01}O_2$,
$Li_{1.04}Ni_{0.60}Co_{0.2}Mn_{0.17}Zr_{0.01}Al_{0.02}O_{1.9}F_{0.1}$,
$Li_{1.07}Ni_{0.60}Co_{0.2}Mn_{0.17}Zr_{0.01}Ti_{0.01}Al_{0.01}O_{1.9}S_{0.1}$,
$Li_{1.02}Ni_{0.60}Co_{0.20}Mn_{0.16}Mg_{0.02}Zr_{0.015}Ti_{0.005}O_{1.9}S_{0.1}$,
$Li_{1.03}Ni_{0.60}Co_{0.20}Mn_{0.18}Ti_{0.01}Al_{0.01}O_{1.9}Cl_{0.1}$,
$Li_{1.05}Ni_{0.60}Co_{0.20}Mn_{0.17}Mg_{0.01}Zr_{0.01}Al_{0.01}O_{1.9}Cl_{0.1}$,
$Li_{1.04}Ni_{0.60}Co_{0.20}Mn_{0.15}Zr_{0.02}Ti_{0.03}O_{1.9}F_{0.1}$,
$Li_{1.09}Ni_{0.60}Co_{0.20}Mn_{0.17}Mg_{0.02}Ti_{0.01}O_{1.95}F_{0.05}$,
$Li_{1.03}Ni_{0.60}Co_{0.20}Mn_{0.15}Mg_{0.03}Ti_{0.02}O_{1.9}S_{0.1}$,
$Li_{1.04}Ni_{0.06}Co_{0.20}Mn_{0.17}Zr_{0.01}Ti_{0.01}Al_{0.01}O_{1.9}S_{0.1}$,
$Li_{1.09}Ni_{0.80}Co_{0.10}Mn_{0.08}Mg_{0.01}Ti_{0.005}Al_{0.005}O_2$,
$Li_{1.085}Ni_{0.80}Co_{0.10}Mn_{0.08}Zr_{0.01}Ti_{0.005}Al_{0.005}O_{1.9}Cl_{0.1}$,
$Li_{1.03}Ni_{0.80}Co_{0.10}Mn_{0.06}Mg_{0.01}Zr_{0.01}Ti_{0.01}Al_{0.01}O_2$,
$Li_{1.04}Ni_{0.80}Co_{0.10}Mn_{0.07}Zr_{0.01}Al_{0.02}O_{1.9}F_{0.1}$,
$Li_{1.07}Ni_{0.80}Co_{0.10}Mn_{0.07}Zr_{0.01}Ti_{0.01}Al_{0.01}O_{1.9}S_{0.1}$,
$Li_{1.02}Ni_{0.80}Co_{0.10}Mn_{0.06}Mg_{0.02}Zr_{0.015}Ti_{0.005}O_{1.9}S_{0.1}$,
$Li_{1.03}Ni_{0.80}Co_{0.10}Mn_{0.08}Ti_{0.01}Al_{0.01}O_{1.9}Cl_{0.1}$,
$Li_{1.05}Ni_{0.80}Co_{0.10}Mn_{0.07}Mg_{0.01}Zr_{0.01}Al_{0.01}O_{1.9}Cl_{0.1}$,
$Li_{1.04}Ni_{0.80}Co_{0.10}Mn_{0.05}Zr_{0.02}Ti_{0.03}O_{1.9}F_{0.1}$,
$Li_{1.09}Ni_{0.80}Co_{0.10}Mn_{0.07}Mg_{0.02}Ti_{0.01}O_{1.95}F_{0.05}$,
$Li_{1.03}Ni_{0.80}Co_{0.10}Mn_{0.05}Mg_{0.03}Ti_{0.02}O_{1.9}S_{0.1}$,
$Li_{1.04}Ni_{0.80}Co_{0.10}Mn_{0.07}Zr_{0.01}Ti_{0.01}Al_{0.01}O_{1.9}S_{0.1}$,
$Li_{1.01}Ni_{0.80}Co_{0.10}Mn_{0.08}Mg_{0.01}Ti_{0.005}Al_{0.005}O_2$,
$Li_{1.05}Ni_{0.80}Co_{0.10}Mn_{0.08}Mg_{0.005}Zr_{0.005}Ti_{0.01}O_{1.9}F_{0.1}$,
$Li_{1.1}Ni_{0.80}Co_{0.10}Mn_{0.05}Mg_{0.01}Zr_{0.01}Al_{0.03}O_2$,
$Li_{1.04}Ni_{0.80}Co_{0.10}Mn_{0.05}Mg_{0.02}Zr_{0.03}O_{1.95}F_{0.05}$,
$Li_{1.06}Ni_{0.80}Co_{0.10}Mn_{0.06}Mg_{0.02}Ti_{0.02}O_2$,
$Li_{1.08}Ni_{0.80}Co_{0.10}Mn_{0.07}Mg_{0.01}Zr_{0.01}Al_{0.01}O_{1.9}S_{0.1}$,
$Li_{1.09}Ni_{0.80}Co_{0.10}Mn_{0.08}Mg_{0.01}Ti_{0.005}Al_{0.005}O_2$,
$Li_{1.085}Ni_{0.80}Co_{0.10}Mn_{0.08}Zr_{0.01}Ti_{0.005}Al_{0.005}O_{1.9}Cl_{0.1}$,
$Li_{1.03}Ni_{0.80}Co_{0.10}Mn_{0.06}Mg_{0.01}Zr_{0.01}Ti_{0.01}Al_{0.01}O_2$,
$Li_{1.04}Ni_{0.80}Co_{0.10}Mn_{0.07}Zr_{0.01}Al_{0.02}O_{1.9}F_{0.1}$,
$Li_{1.07}Ni_{0.80}Co_{0.10}Mn_{0.07}Zr_{0.01}Ti_{0.01}Al_{0.01}O_{1.9}S_{0.1}$,
$Li_{1.02}Ni_{0.80}Co_{0.10}Mn_{0.06}Mg_{0.02}Zr_{0.015}Ti_{0.005}O_{1.9}S_{0.1}$,
$Li_{1.03}Ni_{0.80}Co_{0.10}Mn_{0.08}Ti_{0.01}Al_{0.01}O_{1.9}Cl_{0.1}$,
$Li_{1.05}Ni_{0.80}Co_{0.10}Mn_{0.07}Mg_{0.01}Zr_{0.01}Al_{0.01}O_{1.9}Cl_{0.1}$,
$Li_{1.04}Ni_{0.80}Co_{0.10}Mn_{0.05}Zr_{0.02}Ti_{0.03}O_{1.9}F_{0.1}$,
$Li_{1.09}Ni_{0.80}Co_{0.10}Mn_{0.07}Mg_{0.02}Ti_{0.01}O_{1.95}F_{0.05}$,
$Li_{1.03}Ni_{0.80}Co_{0.10}Mn_{0.05}Mg_{0.03}Ti_{0.02}O_{1.9}S_{0.1}$, and
$Li_{1.04}Ni_{0.80}Co_{0.10}Mn_{0.07}Zr_{0.01}Ti_{0.01}Al_{0.01}O_{1.9}S_{0.1}$.

In the lithium-ion battery according to the present application, a negative electrode active material of the negative electrode sheet can be soft carbon, hard carbon, artificial graphite, natural graphite, silicon, silicon oxygen compound, silicon carbon composite, lithium titanate, metal that can form an alloy with lithium, etc. These negative electrode active materials can be used alone or in combination of two or more.

In the lithium-ion battery according to the present application, the positive electrode sheet further includes a binder and a conductive agent. A positive electrode slurry containing the positive active material, the binder and the conductive agent is coated on a positive electrode current collector, and after the positive electrode slurry is dried, the positive electrode sheet is obtained. The types and contents of the conductive agent and the binder are not specifically limited, and can be selected according to actual needs. The type of the positive electrode current collector is also not specifically limited, and can be selected according to actual needs, and preferably it can be an aluminum foil.

Similarly, the negative electrode sheet further includes a binder and a conductive agent. A negative electrode slurry containing the negative electrode active material, the binder and the conductive agent is coated on a negative electrode current collector, and after the negative electrode slurry is dried, the negative electrode sheet is obtained. The types and contents of the conductive agent and the binder are not specifically limited, and can be selected according to actual needs. The type of the negative electrode current collector is also not specifically limited, and can be selected according to actual needs, and preferably it can be a copper foil.

In the lithium-ion battery according to the present application, the separator is arranged between the positive electrode sheet and the negative electrode sheet to play a role of separation. The type of the separator is not specifically limited, and it can be any separator material used in existing lithium-ion batteries, such as polyethylene, polypropylene, polyvinylidene fluoride and their multilayer composite films, but not limited to these.

In the lithium-ion battery according to the present application, end-of-charge voltage of the lithium-ion battery is not less than 4.2 V, that is, the lithium-ion battery can be used under high voltage not less than 4.2 V. Preferably, the end-of-charge voltage of the lithium-ion battery is not less than 4.35 V.

The lithium-ion battery according to the present application can be a hard-shell lithium-ion battery or a soft-package lithium-ion battery. The hard-shell lithium-ion battery preferably uses a metal hard-shell. The soft-package lithium-ion battery preferably uses a packaging bag as a battery case, the packaging bag usually includes an accommodating portion and a sealing portion, where the accommodating portion is used to accommodate the electrode assembly and the electrolyte, and the sealing portion is used to seal the electrode assembly and the electrolyte. In the present application, an improvement of the performance of the soft-package lithium-ion battery is more obvious, the reason is that the soft-package lithium-ion battery is prone to swelling in use, whereas the present application can greatly reduce gas production in the battery, and avoid shortening the life of the soft-package lithium-ion battery due to swelling.

In the lithium-ion battery according to the present application, in the compounds represented by Formula I-1, Formula I-2, and Formula I-3:

$C_1$-$C_{12}$ alkyl group may be a chain alkyl group or a cyclic alkyl group, the chain alkyl may be a linear alkyl group or a branched alkyl group, hydrogen on a ring of the cyclic alkyl group may be further substituted by an alkyl group. A preferable lower limit of the number of carbon atom in $C_1$-$C_{12}$ alkyl group is 1, 2, 3, 4 or 5, and a preferable upper limit of the same is 3, 4, 5, 6, 8, 10 or 12. Preferably, $C_1$-$C_{10}$ alky group is selected; more preferably, $C_1$-$C_6$ chain alkyl group or $C_3$-$C_8$ cyclic alkyl group is selected; further more preferably, $C_1$-$C_4$ chain alkyl group or $C_5$-$C_7$ cyclic alkyl group is selected. Examples of $C_1$-$C_{12}$ alkyl group specifically include: methyl, ethyl, n-propyl, isopropyl, n-butyl, isobutyl, sec-butyl, tert-butyl, n-pentyl, isopentyl, neopentyl, hexyl, 2-methyl-pentyl, 3-methyl-pentyl, 1,1,2-trimethyl-propyl, 3,3-dimethyl-butyl, heptyl, 2-heptyl, 3-heptyl, 2-methylhexyl, 3-methylhexyl, isoheptyl, octyl, nonyl and decyl.

When the aforementioned $C_1$-$C_{12}$ alkyl group contains an oxygen atom, it may be $C_1$-$C_{12}$ alkoxyl group. Preferably, $C_1$-$C_{10}$ alkoxyl group is selected; more preferably, $C_1$-$C_6$ alkoxyl group is selected; further more preferably, $C_1$-$C_4$ alkoxyl group is selected. Examples of $C_1$-$C_{12}$ alkoxyl group specifically include: methoxy, ethoxy, n-propoxy, isopropoxy, n-butoxy, sec-butoxy, tert-butoxy, n-pentoxy, isopentoxy, cyclopentoxy and cyclohexyloxy.

$C_2$-$C_{12}$ alkenyl group may be a cyclic alkenyl group or a chain alkenyl group, the chain alkenyl group may be a linear alkenyl group or a branched alkenyl group. Additionally, the number of double bond in $C_2$-$C_{12}$ alkenyl group is preferably 1. A preferable lower limit of the number of carbon atom in $C_2$-$C_{12}$ alkenyl group is 2, 3, 4 or 5, and a preferable upper limit of the same is 3, 4, 5, 6, 8, 10 or 12. Preferably, $C_2$-$C_{10}$ alkenyl group is selected; more preferably, $C_2$-$C_6$ alkenyl group is selected; further more preferably, $C_2$-$C_5$ alkenyl group is selected. Examples of $C_2$-$C_{12}$ alkenyl group specifically include: vinyl, allyl, isopropenyl, pentenyl, cyclohexenyl, cycloheptenyl and cyclooctenyl.

$C_2$-$C_{12}$ alkynyl group may be a cyclic alkynyl group or a chain alkynyl group, the chain alkynyl group may be a linear alkynyl group or a branched alkynyl group. Additionally, the number of triple bond in $C_2$-$C_{12}$ alkynyl group is preferably 1. A preferable lower limit of the number of carbon atom in $C_2$-$C_{12}$ alkynyl group is 2, 3, 4 or 5, and a preferable upper limit of the same is 3, 4, 5, 6, 8, 10 or 12. Preferably, $C_2$-$C_{10}$ alkynyl group is selected; more preferably, $C_2$-$C_6$ alkynyl group is selected; further more preferably, $C_2$-$C_5$ alkynyl group is selected. Examples of $C_2$-$C_{12}$ alkynyl group specifically include: ethynyl, propargyl, isopropynyl, pentynyl, cyclohexynyl, cycloheptynyl and cyclooctynyl.

$C_2$-$C_{12}$ amido group may be selected from

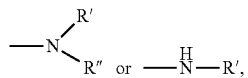

where R' and R" are selected from $C_1$-$C_{12}$ alkyl.

$C_6$-$C_{26}$ aryl group may be phenyl, phenalkyl, biphenyl, or a fused ring aromatic hydrocarbon group (e.g., naphthyl, anthryl, phenanthryl), the biphenyl and the fused ring aromatic hydrocarbon group can be further substituted by alkyl or alkenyl. Preferably, $C_6$-$C_{16}$ aryl group is selected; more preferably, $C_6$-$C_{14}$ aryl group is selected; further more preferably, $C_6$-$C_9$ aryl group is selected. Examples of $C_6$-$C_{26}$ aryl group specifically include: phenyl, benzyl, biphenyl, p-tolyl, o-tolyl, m-tolyl, naphthyl, anthryl, and phenanthryl.

A heteroatom in $C_2$-$C_{12}$ heterocyclyl group can be selected from one or more of oxygen, nitrogen, sulfur, phosphorus, and boron, a heterocycle can be an aliphatic heterocycle or an aromatic heterocycle. Preferably, $C_2$-$C_{10}$ heterocyclyl group is selected; more preferably, $C_2$-$C_7$ heterocyclyl group is selected; further more preferably, five-membered aromatic heterocycle, six-membered aromatic heterocycle and benzoheterocycle are selected. Examples of $C_2$-$C_{12}$ heterocyclyl group specifically include: ethylene oxide group, propylene oxide group, ethylene sulfide group, aziridine group, β-propiolactone group, furyl, thienyl, pyrrolyl, thiazolyl, imidazolyl, pyridyl, pyrazinyl, pyrimidinyl, pyridazinyl, indolyl and quinolyl.

The halogen atom as a substituent can be selected from one or more of a fluorine atom, a chlorine atom, and a bromine atom, preferably fluorine atom.

(1) Specifically, the compound represented by Formula I-1 is a pyrimidine compound with multiple nitrile groups.

In Formula I-1:

Preferably, $R_1$, $R_2$, $R_3$ and $R_4$ each are independently selected from a hydrogen atom, a fluorine atom, a chlorine atom, a bromine atom, a substituted or unsubstituted $C_1$-$C_6$ linear or branched alkyl group, a substituted or unsubstituted $C_5$-$C_9$ cyclic alkyl group, a substituted or unsubstituted $C_1$-$C_6$ alkoxyl group, a substituted or unsubstituted $C_1$-$C_6$ amido group, a substituted or unsubstituted $C_2$-$C_6$ alkenyl group, a substituted or unsubstituted $C_2$-$C_6$ alkynyl group, a substituted or unsubstituted $C_6$-$C_{12}$ aryl group, and a substituted or unsubstituted $C_2$-$C_{12}$ heterocyclyl group; more preferably, $R_1$, $R_2$, $R_3$ and $R_4$ each are independently selected from a hydrogen atom, a fluorine atom, a chlorine atom, a bromine atom, a substituted or unsubstituted $C_1$-$C_3$ linear or branched alkyl group, a substituted or unsubstituted $C_5$-$C_7$ cyclic alkyl group, a substituted or unsubstituted $C_1$-$C_3$ alkoxyl group, a substituted or unsubstituted $C_1$-$C_3$ amido group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, and a substituted or unsubstituted $C_2$-$C_7$ heterocyclyl group. Where a substituent is selected from one or more of halogen atoms.

x is preferably selected from an integer of 0-6, more preferably selected from an integer of 0-4, further more preferably selected from 0, 1 or 2.

y is preferably selected from an integer of 0-6, more preferably selected from an integer of 0-4, further more preferably selected from 0, 1 or 2.

m is preferably selected from 1 or 2.

n is preferably selected from 1 or 2.

Preferably, $R_1$ and $R_3$ are the same group; more preferably, $R_1$, $R_3$ and $R_4$ are the same group.

Preferably, $R_1$ and $R_3$ are hydrogen atoms; more preferably, $R_1$, $R_3$ and $R_4$ are hydrogen atoms.

Preferably, $R_1$, $R_2$, $R_3$ and $R_4$ are hydrogen atoms, or $R_1$, $R_3$ and $R_4$ are hydrogen atoms, while $R_2$ is selected from a fluorine atom, a chlorine atom, a bromine atom, a substituted or unsubstituted $C_1$-$C_6$ linear or branched alkyl group, and a substituted or unsubstituted $C_1$-$C_6$ alkoxyl group. Where a substituent is selected from one or more of halogen atoms, preferably, the substituent is selected from a fluorine atom.

Preferably, the compound represented by Formula I-1 can be specifically selected from one or more of the following compounds, but the present application is not limited thereto:

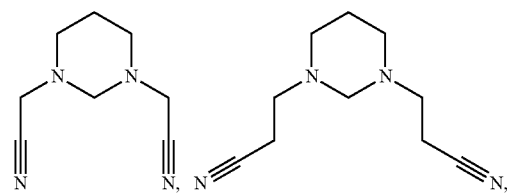

-continued

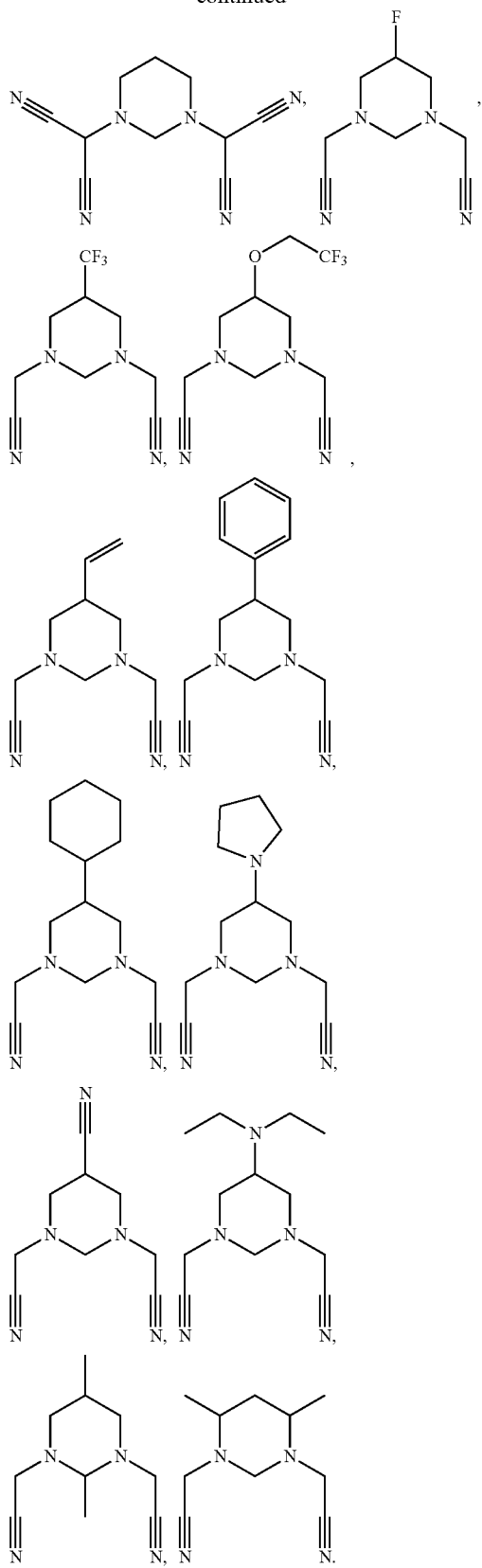

(2) Specifically, the compound represented by Formula I-2 is a piperazine compound with multiple nitrile groups.

In Formula I-2:

Preferably, $R_1$, $R_2$, $R_3$ and $R_4$ each are independently selected from a hydrogen atom, a fluorine atom, a chlorine atom, a bromine atom, a substituted or unsubstituted $C_1$-$C_6$ linear or branched alkyl group, a substituted or unsubstituted $C_5$-$C_9$ cyclic alkyl group, a substituted or unsubstituted $C_1$-$C_6$ alkoxyl group, a substituted or unsubstituted $C_1$-$C_6$ amido group, a substituted or unsubstituted $C_2$-$C_6$ alkenyl group, a substituted or unsubstituted $C_2$-$C_6$ alkynyl group, a substituted or unsubstituted $C_6$-$C_{12}$ aryl group, and a substituted or unsubstituted $C_2$-$C_{12}$ heterocyclyl group; more preferably, $R_1$, $R_2$, $R_3$ and $R_4$ each are independently selected from a hydrogen atom, a fluorine atom, a chlorine atom, a bromine atom, a substituted or unsubstituted $C_1$-$C_3$ linear or branched alkyl group, a substituted or unsubstituted $C_5$-$C_7$ cyclic alkyl group, a substituted or unsubstituted $C_1$-$C_3$ alkoxyl group, a substituted or unsubstituted $C_1$-$C_3$ amido group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, and a substituted or unsubstituted $C_2$-$C_7$ heterocyclyl group. Where a substituent is selected from one or more of halogen atoms.

x is preferably selected from an integer of 0-6, more preferably selected from an integer of 0-4, further more preferably selected from 0, 1 or 2.

y is preferably selected from an integer of 0-6, more preferably selected from an integer of 0-4, further more preferably selected from 0, 1 or 2.

m is preferably selected from 1 or 2.

n is preferably selected from 1 or 2.

Preferably, at least two of $R_1$, $R_2$, $R_3$ and $R_4$ are the same group, and more preferably, at least three of $R_1$, $R_2$, $R_3$ and $R_4$ are the same group.

Preferably, at least two of $R_1$, $R_2$, $R_3$ and $R_4$ are hydrogen atoms; more preferably, at least three of $R_1$, $R_2$, $R_3$ and $R_4$ are hydrogen atoms.

Preferably, $R_1$, $R_2$, $R_3$ and $R_4$ are hydrogen atoms, or three of $R_1$, $R_2$, $R_3$ and $R_4$ are hydrogen atoms, and the remaining one is selected from a fluorine atom, a chlorine atom, a bromine atom, a substituted or unsubstituted $C_1$-$C_6$ linear or branched alkyl group, and a substituted or unsubstituted $C_1$-$C_6$ alkoxyl group. Where a substituent is selected from one or more of halogen atoms, and preferably, the substituent is selected from a fluorine atom.

Preferably, the compound represented by Formula I-2 can be specifically selected from one or more of the following compounds, but the present application is not limited thereto:

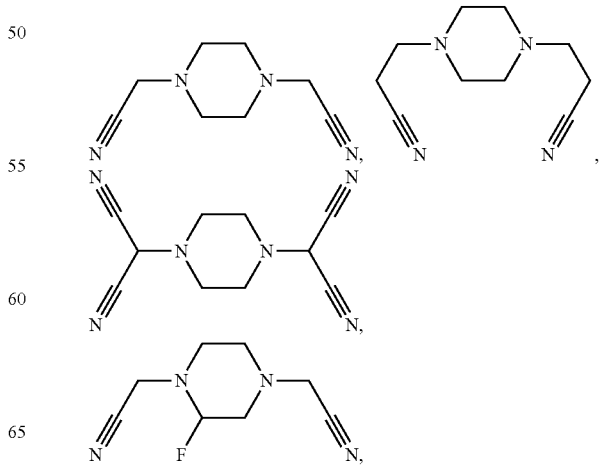

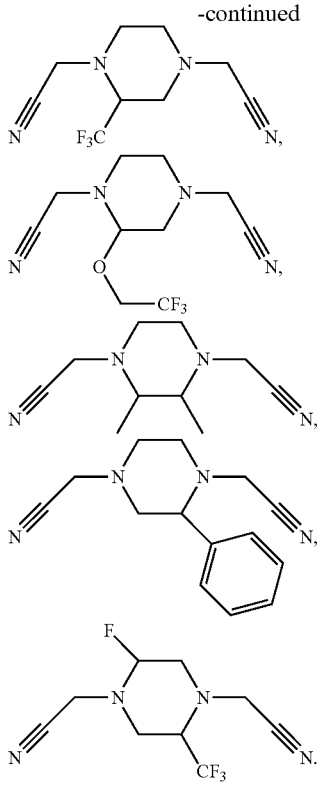

(3) Specifically, the compound represented by Formula I-3 is a s-triazine compound with multiple nitrile groups.

In Formula I-3:

Preferably, $R_1$, $R_2$ and $R_3$ each are independently selected from a hydrogen atom, a fluorine atom, a chlorine atom, a bromine atom, a substituted or unsubstituted $C_1$-$C_6$ linear or branched alkyl group, a substituted or unsubstituted $C_5$-$C_9$ cyclic alkyl group, a substituted or unsubstituted $C_1$-$C_6$ alkoxyl group, a substituted or unsubstituted $C_1$-$C_6$ amido group, a substituted or unsubstituted $C_2$-$C_6$ alkenyl group, a substituted or unsubstituted $C_2$-$C_6$ alkynyl group, a substituted or unsubstituted $C_6$-$C_{12}$ aryl group, and a substituted or unsubstituted $C_2$-$C_{12}$ heterocyclyl group; more preferably, $R_1$, $R_2$ and $R_3$ each are independently selected from a hydrogen atom, a fluorine atom, a chlorine atom, a bromine atom, a substituted or unsubstituted $C_1$-$C_3$ linear or branched alkyl group, a substituted or unsubstituted $C_5$-$C_7$ cyclic alkyl group, a substituted or unsubstituted $C_1$-$C_3$ alkoxyl group, a substituted or unsubstituted $C_1$-$C_3$ amido group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, and a substituted or unsubstituted $C_2$-$C_7$ heterocyclyl group. Where a substituent is selected from one or more of halogen atoms.

x is preferably selected from an integer of 0-6, more preferably selected from an integer of 0-4, and further more preferably selected from 0, 1 or 2.

y is preferably selected from an integer of 0-6, more preferably selected from an integer of 0-4, and further more preferably selected from 0, 1 or 2.

z is preferably selected from an integer of 0-6, more preferably selected from an integer of 0-4, and further more preferably selected from 0, 1 or 2.

m is preferably selected from 1 or 2.

n is preferably selected from 1 or 2.

k is preferably selected from 1 or 2.

Preferably, at least two of $R_1$, $R_2$ and $R_3$ are the same group.

Preferably, at least two of $R_1$, $R_2$ and $R_3$ are hydrogen atoms.

Preferably, $R_1$, $R_2$ and $R_3$ are hydrogen atoms, or two of $R_1$, $R_2$ and $R_3$ are hydrogen atoms, and the remaining one is selected from a fluorine atom, a chlorine atom, a bromine atom, a substituted or unsubstituted $C_1$-$C_6$ linear or branched alkyl group, and a substituted or unsubstituted $C_1$-$C_6$ alkoxyl group. Where a substituent is selected from one or more of halogen atoms, and preferably, the substituent is selected from a fluorine atom.

Preferably, the compound represented by Formula I-3 can be specifically selected from one or more of the following compounds, but the present application is not limited thereto:

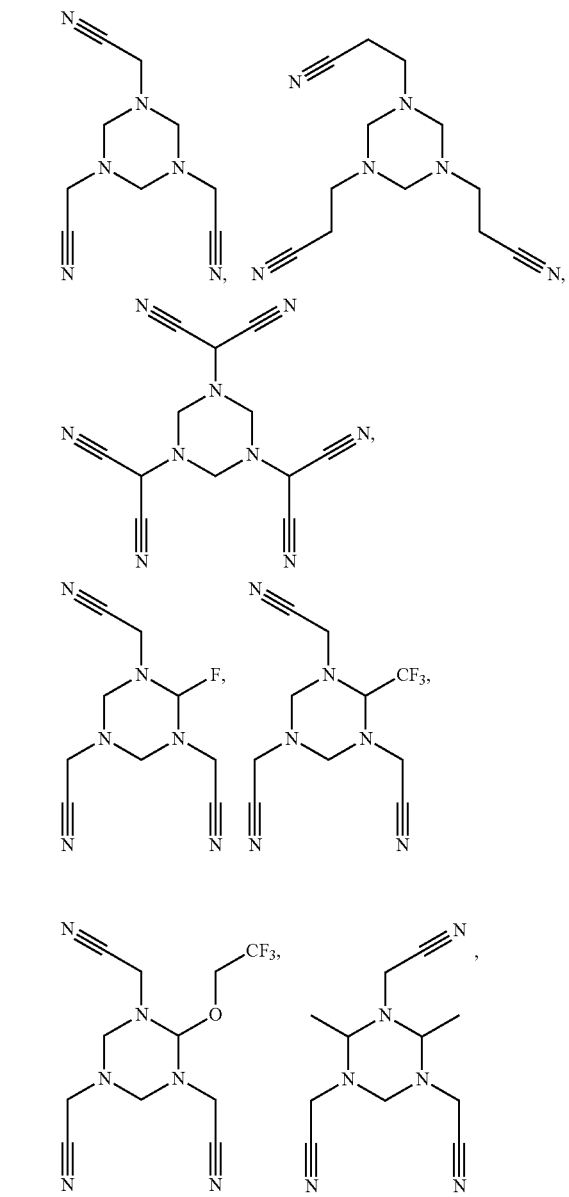

-continued

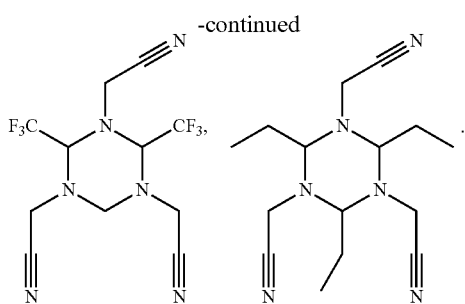

In the lithium-ion battery according to the present application, the additive A can be synthesized by the following method.

(1) Preparation of the Compound Represented by Formula I-1

A reaction scheme is as follows:

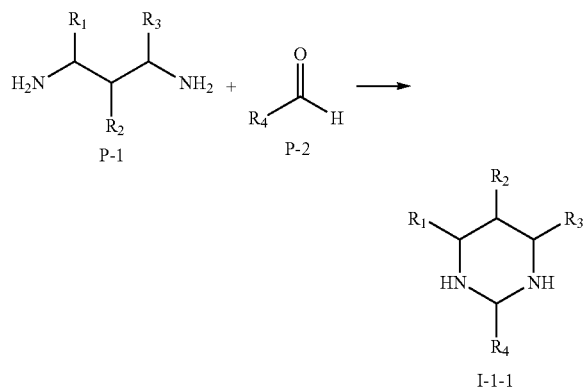

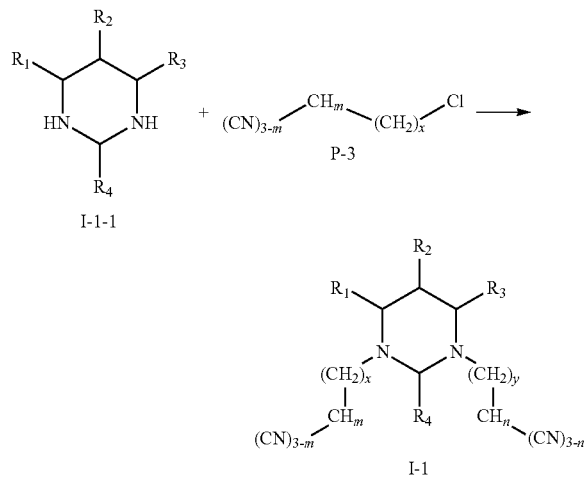

A specific preparation process is:

A P-2 aqueous solution with a concentration of 30%-40% is added dropwise into a raw material P-1 within 20 min-60 min and stirred rapidly, and after the addition is completed, stirring is performed rapidly for 15 h-30 h, and refluxing and stirring are performed in an oil bath at 70° C.-90° C. for 3 h-5 h, so as to obtain a colorless smoky viscous liquid as an intermediate product I-1-1; $K_2CO_3$, KI and anhydrous acetonitrile are added subsequently, stirring is performed rapidly to form a solid-liquid mixed phase, and a raw material P-3 is rapidly added at 40° C.-60° C., stirring is continued for 10 h-20 h before cooling to room temperature, separating and purifying, so as to obtain the compound represented by Formula I-1.

(2) Preparation of the Compound Represented by Formula I-2

A reaction scheme is as follows:

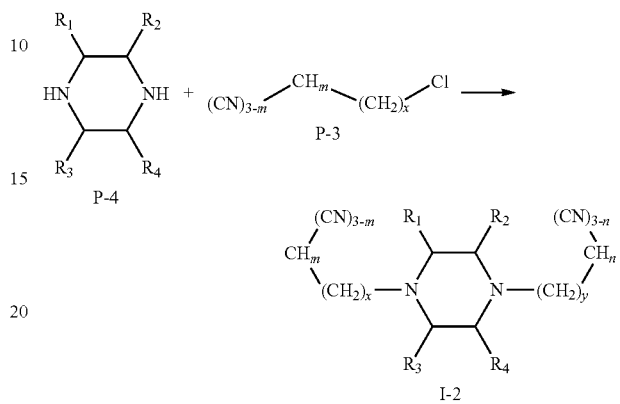

A specific preparation process is:

Anhydrous sodium carbonate, a raw material P-4 and a raw material P-3 are mixed in absolute ethanol, the reaction are performed for 2 h-5 h under stirring; hot ethanol is used to rinse repeatedly to obtain a crude product, which is subjected to recrystallization, to obtain the compound represented by Formula I-2.

(3) Preparation of the Compound Represented by Formula I-3

A reaction scheme is as follows:

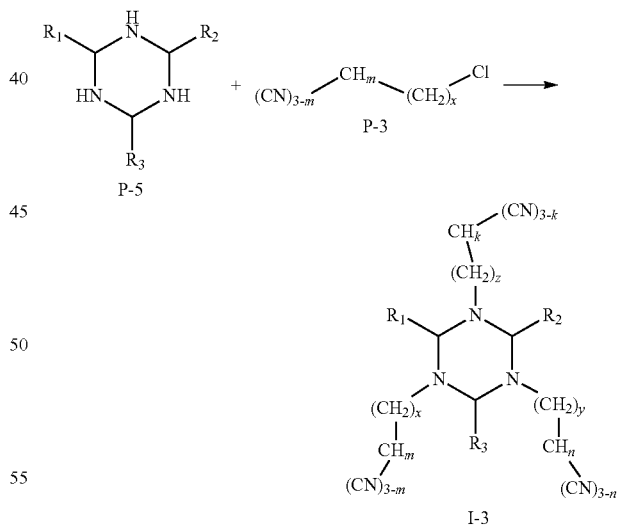

A specific preparation process is:

Anhydrous sodium carbonate, a raw material P-5 and a raw material P-3 are mixed in absolute ethanol, the reaction is performed for 2 h-5 h under stirring; hot ethanol is used to rinse repeatedly to obtain a crude product, which is subjected to recrystallization, to obtain the compound represented by Formula I-3.

In some embodiments, the lithium-ion battery can include an outer package for packaging a positive electrode sheet, a negative electrode sheet, and an electrolyte. As an example, the positive electrode sheet, the negative electrode sheet, and the separator can be laminated or wound to form an electrode assembly with a laminated structure or an electrode assembly with a wound structure, the electrode assembly is packaged in the outer package; the electrolyte can adopt an electrolyte, and the electrolyte is immersed in the electrode assembly. The number of the electrode assembly in the lithium-ion battery can be one or several, and can be adjusted according to requirements.

In some embodiments, the outer package of the lithium-ion battery can be a soft-package, such as a bag-type soft-package. The material of the soft-package can be plastics, for example, it can include one or more of polypropylene (PP), polybutylene terephthalate (PBT), polybutylene succinate (PBS), etc. The outer package of the lithium-ion battery can also be a hard-shell, such as aluminium case, etc.

Figure 4:
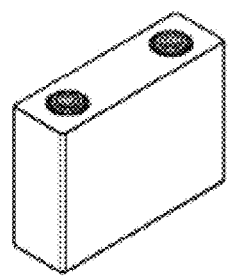
FIG. 4 is a schematic diagram of an embodiment of a lithium-ion battery.

The shape of the lithium-ion battery has no particular limitation in present application, and can be a cylinder, a square or any other shape. FIG. 4 is an example of a lithium-ion battery 5 with a square structure.

In some embodiments, the lithium-ion battery can be assembled into a battery module, and the number of the lithium-ion battery included in the battery module can be multiple, and the specific number can be adjusted according to the application and capacity of the battery module.

Figure 5:
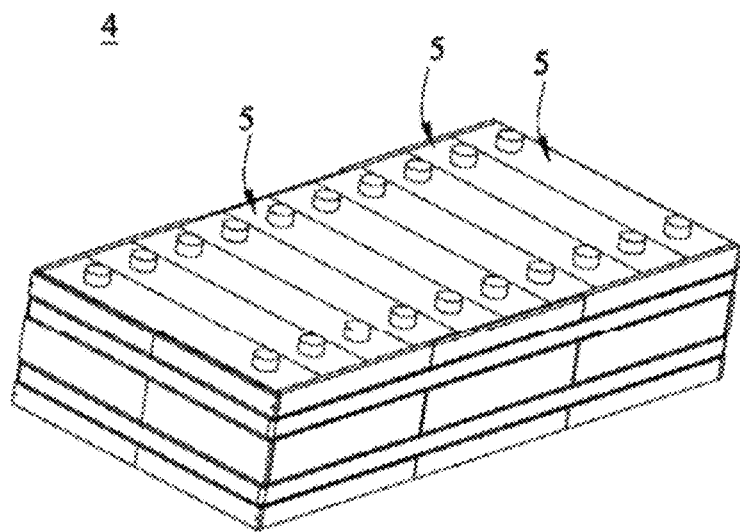
FIG. 5 is a schematic diagram of an embodiment of a battery module.

FIG. 5 is an example of a battery module 4. Referring to FIG. 5, in the battery module 4, a plurality of lithium-ion batteries 5 can be arranged in sequence along the length direction of the battery module 4. Of course, they can also be arranged in any other way. Further, the plurality of lithium-ion batteries 5 can be secured by fasteners.

Optionally, the battery module 4 can further include a shell with an accommodation space, and the plurality of lithium-ion batteries 5 are accommodated in the accommodation space.

In some embodiments, the above battery module can also be assembled into a battery pack, and the number of battery module included in the battery pack can be adjusted according to the application and capacity of the battery pack.

Figure 6:
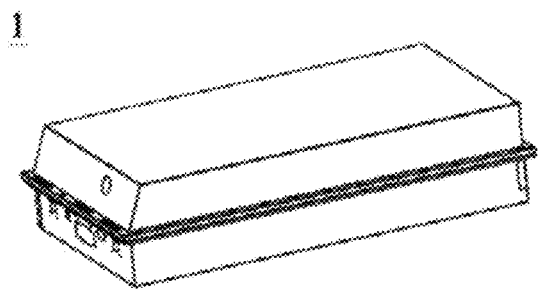
FIG. 6 is a schematic diagram of an embodiment of a battery pack.
Figure 7:
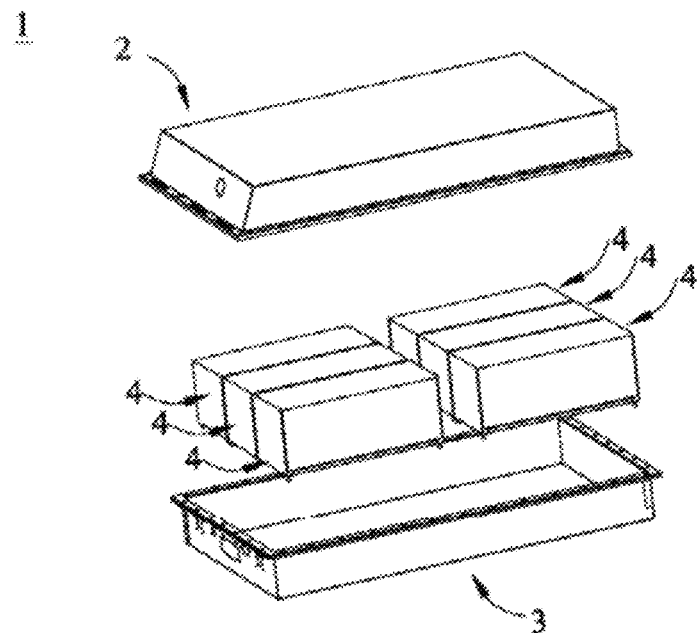
FIG. 7 is an exploded view of FIG. 6.

FIG. 6 and FIG. 7 are illustrated as examples of a battery pack 1. Referring to FIG. 6 and FIG. 7, the battery pack 1 can include a battery box and a plurality of battery modules 4 arranged in the battery box. The battery box includes an upper box body 2 and a lower box body 3, the upper box body 2 can cover on the lower box body 3, so as to form an enclosed space for accommodating the battery modules 4. The plurality of battery modules 4 can be arranged in the battery box in any way.

The apparatus of the second aspect of the present application will be described as follows.

The second aspect of the present application provides an apparatus, the apparatus includes the lithium-ion battery according to the first aspect of the present application, the lithium-ion battery provides power source for the apparatus. The apparatus can be, but not limited to, a mobile apparatus (e.g., a mobile phone, a notebook computer, etc.), an electric vehicle (e.g., a pure electric vehicle, a hybrid electric vehicle, a plug-in hybrid electric vehicle, an electric bicycle, an electric scooter, an electric golf cart, an electric truck, etc.), an electric train, a ship and a satellite, an energy storage system, etc.

The apparatus can be selected as a lithium-ion battery, a battery module, or a battery pack according to its usage requirements.

Figure 8:
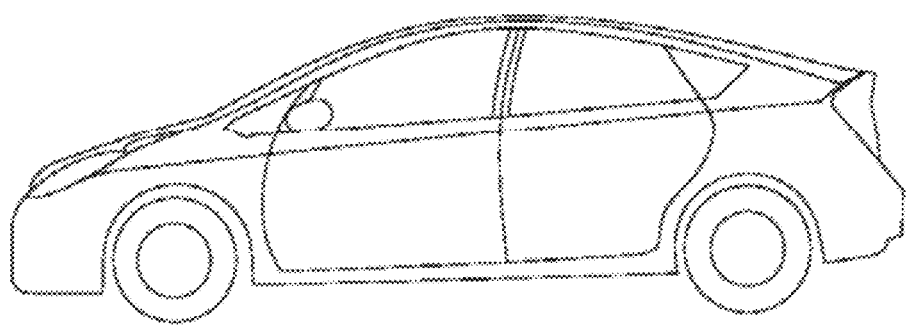
FIG. 8 is a schematic diagram of an embodiment of an apparatus using a lithium-ion battery as a power supply.

FIG. 8 is an example of an apparatus. The apparatus is a pure electric vehicle, a hybrid electric vehicle, or a plug-in hybrid electric vehicle, etc. In order to meet the requirement of the apparatus for high power and high energy density of the lithium-ion battery, a battery pack or a battery module can be used.

As another example, the apparatus can be a mobile phone, a tablet computer, a notebook computer, etc. The apparatus is usually required to be thin and light, and can use lithium-ion battery as a power source.

In order to make purposes, technical solutions and beneficial technical effects of the present application more explicit, the present application will be further described in detail below in conjunction with embodiments. It should be understood that the embodiments described in the description are only for illustrating the present application, not for limiting the present application, formulations and ratios in the embodiments can be selected according to specific conditions and have no substantial effect on the results.

In examples and comparative examples, reagents, materials, and instruments used are all commercially available unless otherwise specified. Where specific synthesis processes of additives A1, A2 and A3 are as follows, other types of additives A can be synthesized according to similar methods.

Synthesis of an Additive A1:

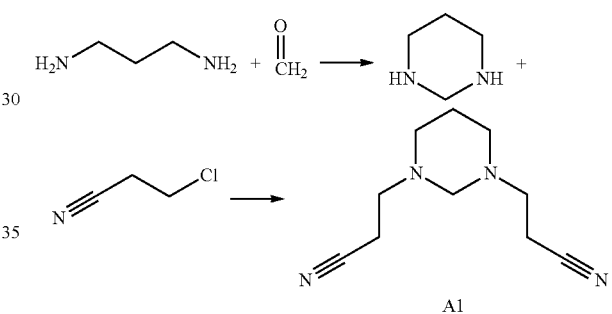

Within 0.5 h, 37% of aqueous formaldehyde solution is added dropwise into 1,3-propanediamine and stirred rapidly, and after the addition is completed, rapid stirring is continued for 20 h, then refluxing and stirring are performed at 80° C. in an oil bath for 4 h, so as to obtain a colorless smoky viscous liquid as an intermediate product hexahydro pyrimidine; $K_2CO_3$, KI and anhydrous acetonitrile are added subsequently, stirring is performed rapidly to form a solid-liquid mixed phase, and then β-chloropropylnitrile is added at 60° C. in 0.5 h, stirring is continued for 17 h before cooling to room temperature, separating and purifying, so as to obtain A1. A carbon nuclear magnetic resonance spectrum is shown in FIG. 1.

Synthesis of an Additive A2:

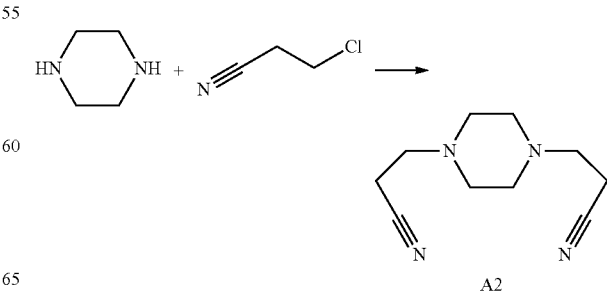

Figure 2:
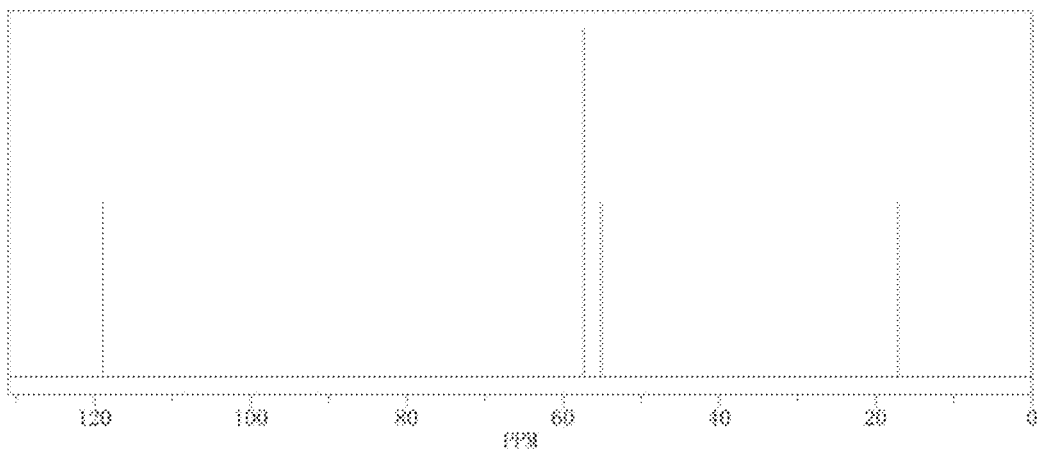
FIG. 2 is a carbon nuclear magnetic resonance spectrum of a compound A2.

Anhydrous sodium carbonate, piperazine and β-chloropropylnitrile are mixed in absolute ethanol, the reaction is performed for 4 h under stirring; hot ethanol is used for rinsing repeatedly to obtain a crude product, which is subjected to recrystallization, so as to obtain A2. A carbon nuclear magnetic resonance spectrum is shown in FIG. 2.

Synthesis of an Additive A3:

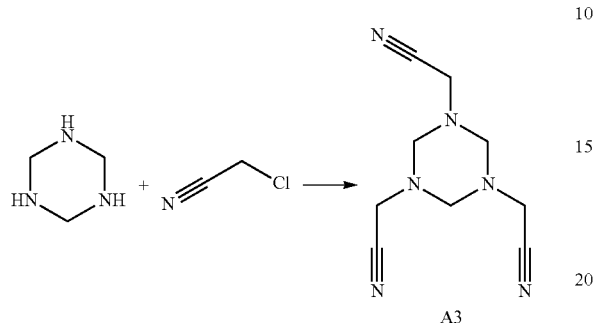

Figure 3:
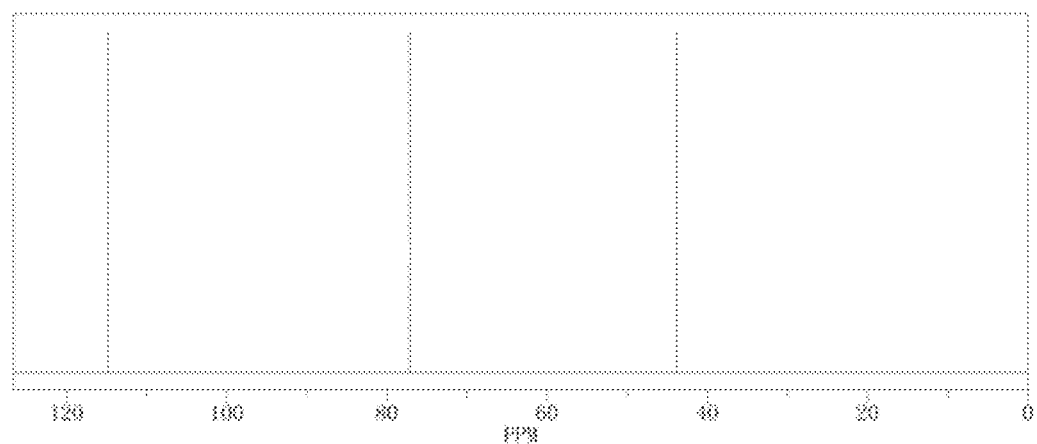
FIG. 3 is a carbon nuclear magnetic resonance spectrum of a compound A3.

Anhydrous sodium carbonate, 1,3,5-s-triazine and chloroacetonitrile are mixed in absolute ethanol, the reaction is performed for 4 h under stirring; hot ethanol is used for rinsing repeatedly to obtain a crude product, which is subjected to recrystallization, so as to obtain A3. A carbon nuclear magnetic resonance spectrum is shown in FIG. 3.

In Examples 1-30 and Comparative Examples 1-2, lithium-ion batteries are prepared according to the following method.

(1) Preparation of an electrolyte

A mixed liquid of ethylene carbonate (abbreviated as EC), ethyl methyl carbonate (abbreviated as EMC), and diethyl carbonate (abbreviated as DEC) is used as an organic solvent, where a mass ratio of EC, EMC and DEC is 1:1:1. A lithium salt is $LiPF_6$, a content of $LiPF_6$ is 12.5% of a total mass of the electrolyte. The additives are added according to electrolyte composition shown in Table 1, where the content of each additive component is calculated relative to the total mass of the electrolyte.

Where additives A used in Examples and Comparative Examples are abbreviated as follows:

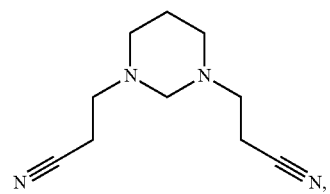

A1

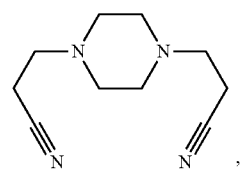

A2

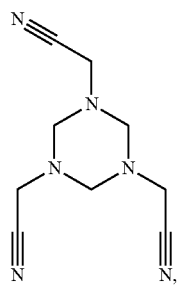

A3

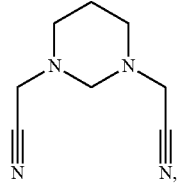

A4

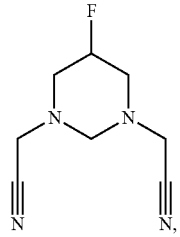

A5

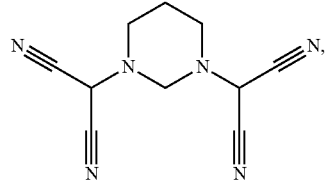

A6

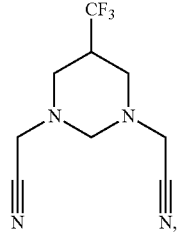

A7

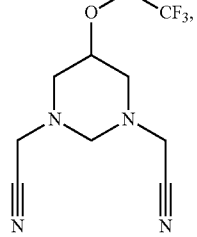

A8

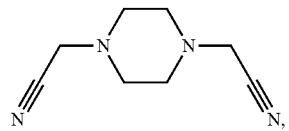

A9

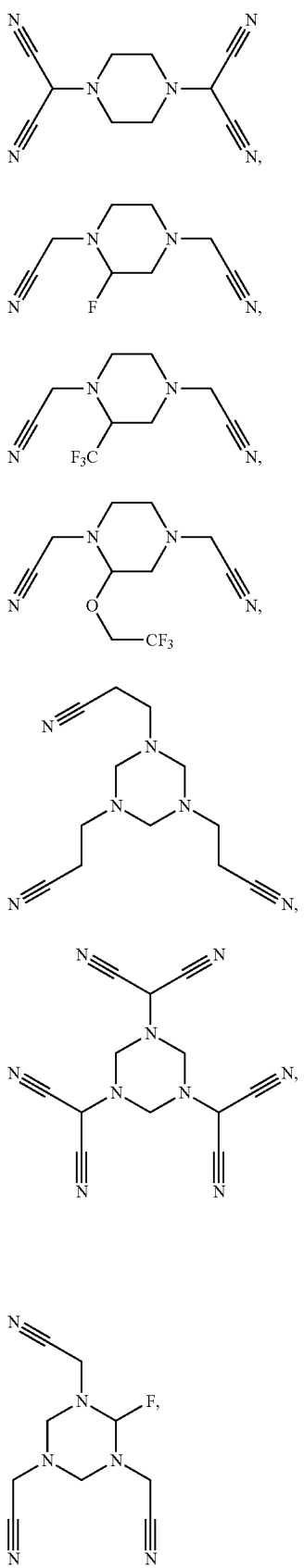
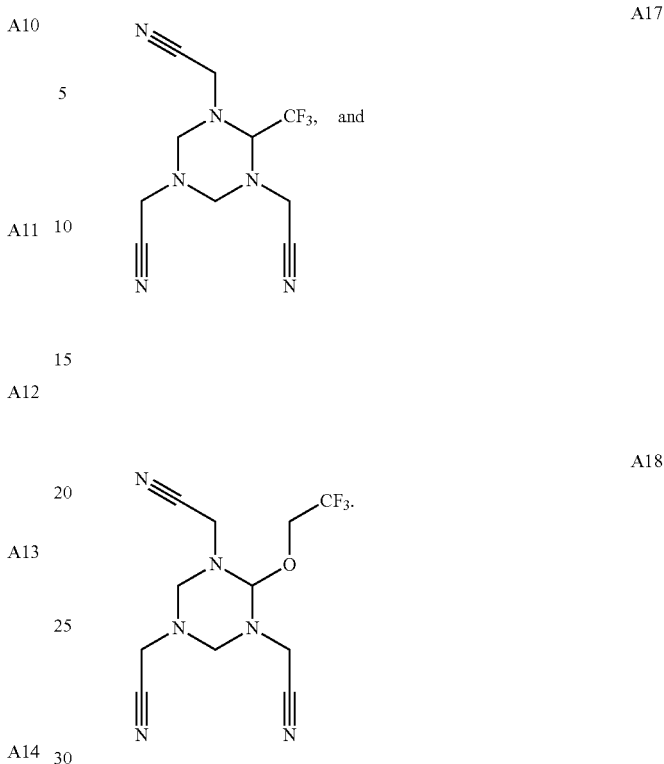

(2) Preparation of a Positive Electrode Sheet

A positive active material, a binder PVDF, and a conductive agent acetylene black, as shown in Table 2, are mixed according to a mass ratio of 98:1:1, and N-methyl pyrrolidone is added, stirring under the action of a vacuum stirrer until it is stable and uniform, so as to obtain a positive electrode slurry; the positive electrode slurry is uniformly coated on an aluminum foil, and after drying at room temperature, the aluminum foil is transferred to a blast oven for drying at 120° C. for 1 h, and then subjected to cold pressing and slitting, so as to obtain the positive electrode sheet.

(3) Preparation of a Negative Electrode Sheet

A negative electrode active material graphite, a conductive agent acetylene black, a thickener sodium carboxymethyl cellulose and a binder styrene-butadiene rubber are mixed according to a mass ratio of 97:1:1:1, deionized water is added, stirring under the action of a vacuum stirrer until it is stable and uniform, so as to obtain a negative electrode slurry; the negative electrode slurry is uniformly coated on a copper foil, and after drying at room temperature, the copper foil is transferred to a blast oven for drying at 120° C. for 1 h, and then subjected to cold pressing and slitting, so as to obtain the negative electrode sheet.

(4) Preparation of a Lithium-Ion Battery

The positive electrode sheet, the negative electrode sheet and the PP/PE/PP separator are wound to obtain an electrode assembly, and the electrode assembly is put into a packaging bag aluminium-plastic film, and then the electrolyte is injected, and then sealing, standing, hot and cold pressing, forming, exhausting, capacity testing and other processes are performed in sequence, so as to obtain the lithium-ion battery.

TABLE 1

Parameters of electrolyte of Examples 1-30 and Comparative Examples 1-2

|  | Additive A | | Additive B | | Additive C | |
| --- | --- | --- | --- | --- | --- | --- |
|  | Type | Content | Type | Content | Type | Content |
| Example 1 | A1 | 0.1% | / | / | / | / |
| Example 2 | A1 | 1.0% | / | / | / | / |
| Example 3 | A1 | 2.0% | / | / | / | / |
| Example 4 | A1 | 3.5% | / | / | / | / |
| Example 5 | A1 | 6.0% | / | / | / | / |
| Example 6 | A1 | 8.0% | / | / | / | / |
| Example 7 | A1 | 10.0% | / | / | / | / |
| Example 8 | A2 | 2.0% | / | / | / | / |
| Example 9 | A3 | 2.0% | / | / | / | / |
| Example 10 | A4 | 2.0% | / | / | / | / |
| Example 11 | A5 | 2.0% | / | / | / | / |
| Example 12 | A6 | 2.0% | / | / | / | / |
| Example 13 | A7 | 2.0% | / | / | / | / |
| Example 14 | A8 | 2.0% | / | / | / | / |
| Example 15 | A9 | 2.0% | / | / | / | / |
| Example 16 | A10 | 2.0% | / | / | / | / |
| Example 17 | A11 | 2.0% | / | / | / | / |
| Example 18 | A12 | 2.0% | / | / | / | / |
| Example 19 | A13 | 2.0% | / | / | / | / |
| Example 20 | A14 | 2.0% | / | / | / | / |
| Example 21 | A15 | 2.0% | / | / | / | / |
| Example 22 | A16 | 2.0% | / | / | / | / |
| Example 23 | A17 | 2.0% | / | / | / | / |
| Example 24 | A18 | 2.0% | / | / | / | / |
| Example 25 | A1 | 2.0% | $LiBF_4$ | 2.0% | / | / |
| Example 26 | A2 | 2.0% | $LiBF_4$ | 2.0% | / | / |
| Example 27 | A3 | 2.0% | $LiBF_4$ | 2.0% | / | / |
| Example 28 | A1 | 2.0% | / | / | VC | 2.0% |
| Example 29 | A2 | 2.0% | / | / | FEC | 2.0% |
| Example 30 | A3 | 2.0% | / | / | PS | 2.0% |
| Comparative Example 1 | / | / | / | / | / | / |
| Comparative Example 2 | Adiponitrile | 2.0% | / | / | / | / |

TABLE 2

Parameters of positive active material of Examples 1-30 and Comparative Examples 1-2

| | Positive Active Material | | Mass ratio of the two |
| --- | --- | --- | --- |
| | Lithium Cobalt Oxide Material | Ternary Material | |
| Example 1 | $Li_{1.01}Co_{0.98}Mg_{0.01}Ti_{0.005}Al_{0.005}O_2$ | $Li_{1.01}Ni_{0.33}Co_{0.33}Mn_{0.31}Mg_{0.01}Ti_{0.005}Al_{0.005}O_2$ | 70:30 |
| Example 2 | $Li_{1.01}Co_{0.98}Mg_{0.01}Ti_{0.005}Al_{0.005}O_2$ | $Li_{1.01}Ni_{0.33}Co_{0.33}Mn_{0.31}Mg_{0.01}Ti_{0.005}Al_{0.005}O_2$ | 70:30 |
| Example 3 | $Li_{1.01}Co_{0.98}Mg_{0.01}Ti_{0.005}Al_{0.005}O_2$ | $Li_{1.01}Ni_{0.33}Co_{0.33}Mn_{0.31}Mg_{0.01}Ti_{0.005}Al_{0.005}O_2$ | 70:30 |
| Example 4 | $Li_{1.01}Co_{0.98}Mg_{0.01}Ti_{0.005}Al_{0.005}O_2$ | $Li_{1.01}Ni_{0.33}Co_{0.33}Mn_{0.31}Mg_{0.01}Ti_{0.005}Al_{0.005}O_2$ | 70:30 |
| Example 5 | $Li_{1.01}Co_{0.98}Mg_{0.01}Ti_{0.005}Al_{0.005}O_2$ | $Li_{1.01}Ni_{0.33}Co_{0.33}Mn_{0.31}Mg_{0.01}Ti_{0.005}Al_{0.005}O_2$ | 70:30 |
| Example 6 | $Li_{1.01}Co_{0.98}Mg_{0.01}Ti_{0.005}Al_{0.005}O_2$ | $Li_{1.01}Ni_{0.33}Co_{0.33}Mn_{0.31}Mg_{0.01}Ti_{0.005}Al_{0.005}O_2$ | 70:30 |
| Example 7 | $Li_{1.01}Co_{0.98}Mg_{0.01}Ti_{0.005}Al_{0.005}O_2$ | $Li_{1.01}Ni_{0.33}Co_{0.33}Mn_{0.31}Mg_{0.01}Ti_{0.005}Al_{0.005}O_2$ | 70:30 |
| Example 8 | $Li_{1.085}Co_{0.98}Zr_{0.01}Ti_{0.005}Al_{0.005}O_{1.9}Cl_{0.1}$ | $Li_{1.01}Ni_{0.50}Co_{0.20}Mn_{0.28}Mg_{0.01}Ti_{0.005}Al_{0.005}O_2$ | 90:10 |
| Example 9 | $Li_{1.03}Co_{0.96}Mg_{0.01}Zr_{0.01}Ti_{0.01}Al_{0.01}O_2$ | $Li_{1.06}Ni_{0.50}Co_{0.20}Mn_{0.26}Mg_{0.02}Ti_{0.02}O_2$ | 87:13 |
| Example 10 | $Li_{1.04}Co_{0.97}Zr_{0.01}Al_{0.02}O_{1.9}F_{0.1}$ | $Li_{1.04}Ni_{0.50}Co_{0.20}Mn_{0.25}Mg_{0.02}Zr_{0.03}O_{1.95}F_{0.05}$ | 84:16 |
| Example 11 | $Li_{1.07}Co_{0.97}Zr_{0.01}Ti_{0.01}Al_{0.01}O_{1.9}S_{0.1}$ | $Li_{1.06}Ni_{0.50}Co_{0.20}Mn_{0.26}Mg_{0.02}Ti_{0.02}O_2$ | 81:19 |
| Example 12 | $Li_{1.02}Co_{0.96}Mg_{0.02}Zr_{0.015}Ti_{0.005}O_{1.9}S_{0.1}$ | $Li_{1.08}Ni_{0.50}Co_{0.20}Mn_{0.27}Mg_{0.01}Zr_{0.01}Al_{0.01}O_{1.9}S_{0.1}$ | 78:22 |
| Example 13 | $Li_{1.03}Co_{0.98}Ti_{0.01}Al_{0.01}O_{1.9}Cl_{0.1}$ | $Li_{1.08}Ni_{0.50}Co_{0.20}Mn_{0.27}Mg_{0.01}Zr_{0.01}Al_{0.01}O_{1.9}S_{0.1}$ | 75:25 |
| Example 14 | $Li_{1.05}Co_{0.97}Zr_{0.01}Al_{0.01}O_{1.9}Cl_{0.1}$ | $Li_{1.04}Ni_{0.50}Co_{0.20}Mn_{0.25}Mg_{0.02}Zr_{0.03}O_{1.95}F_{0.05}$ | 73:27 |
| Example 15 | $Li_{1.04}Co_{0.95}Zr_{0.02}Ti_{0.03}O_{1.9}F_{0.1}$ | $Li_{1.085}Ni_{0.60}Co_{0.20}Mn_{0.18}Zr_{0.01}Ti_{0.005}Al_{0.005}O_{1.9}Cl_{0.1}$ | 71:29 |
| Example 16 | $Li_{1.09}Co_{0.97}Mg_{0.02}Ti_{0.01}O_{1.95}F_{0.05}$ | $Li_{1.07}Ni_{0.60}Co_{0.20}Mn_{0.17}Zr_{0.01}Ti_{0.01}Al_{0.01}O_{1.9}S_{0.1}$ | 70.5:29.5 |
| Example 17 | $Li_{1.03}Co_{0.95}Mg_{0.03}Ti_{0.02}O_{1.9}S_{0.1}$ | $Li_{1.02}Ni_{0.60}Co_{0.20}Mn_{0.16}Mg_{0.02}Zr_{0.015}Ti_{0.005}O_{1.9}$ | 69:31 |
| Example 18 | $Li_{1.04}Co_{0.97}Zr_{0.01}Ti_{0.01}Al_{0.01}O_{1.9}S_{0.1}$ | $Li_{1.05}Ni_{0.60}Co_{0.20}Mn_{0.17}Mg_{0.01}Zr_{0.01}Al_{0.01}O_{1.9}Cl_{0.1}$ | 67:33 |
| Example 19 | $Li_{1.05}Co_{0.98}Mg_{0.005}Zr_{0.005}Ti_{0.01}O_{1.9}F_{0.1}$ | $Li_{1.09}Ni_{0.60}Co_{0.20}Mn_{0.17}Mg_{0.02}Ti_{0.01}O_{1.95}F_{0.05}$ | 65:35 |
| Example 20 | $Li_{1.03}Co_{0.96}Mg_{0.01}Zr_{0.01}Ti_{0.01}Al_{0.01}O_2$ | $Li_{1.03}Ni_{0.60}Co_{0.20}Mn_{0.15}Mg_{0.03}Ti_{0.02}O_{1.9}S_{0.1}$ | 62:38 |
| Example 21 | $Li_{1.07}Co_{0.97}Zr_{0.01}Ti_{0.01}Al_{0.01}O_{1.9}S_{0.1}$ | $Li_{1.04}Ni_{0.60}Co_{0.2}Mn_{0.17}Zr_{0.01}Ti_{0.01}Al_{0.01}O_{1.9}S_{0.1}$ | 59:41 |
| Example 22 | $Li_{1.085}Co_{0.98}Zr_{0.01}Ti_{0.005}Al_{0.005}O_{1.9}Cl_{0.1}$ | $Li_{1.01}Ni_{0.60}Co_{0.20}Mn_{0.18}Mg_{0.01}Ti_{0.005}Al_{0.005}O_2$ | 56:44 |
| Example 23 | $Li_{1.04}Co_{0.95}Zr_{0.02}Ti_{0.03}O_{1.9}F_{0.1}$ | $Li_{1.05}Ni_{0.60}Co_{0.20}Mn_{0.18}Mg_{0.005}Zr_{0.005}Ti_{0.01}O_{1.9}F_{0.1}$ | 53:47 |
| Example 24 | $Li_{1.07}Co_{0.97}Zr_{0.01}Ti_{0.01}Al_{0.01}O_{1.9}S_{0.1}$ | $Li_{1.05}Ni_{0.60}Co_{0.20}Mn_{0.15}Mg_{0.01}Zr_{0.01}Al_{0.03}O_2$ | 50:50 |
| Example 25 | $Li_{1.05}Co_{0.98}Mg_{0.005}Zr_{0.005}Ti_{0.01}O_{1.9}F_{0.1}$ | $Li_{1.04}Ni_{0.60}Co_{0.20}Mn_{0.15}Mg_{0.02}Zr_{0.03}O_{1.95}F_{0.05}$ | 70:30 |
| Example 26 | $Li_{1.04}Co_{0.95}Mg_{0.02}Zr_{0.03}O_{1.95}F_{0.05}$ | $Li_{1.09}Ni_{0.80}Co_{0.10}Mn_{0.08}Mg_{0.01}Ti_{0.005}Al_{0.005}O_2$ | 70:30 |
| Example 27 | $Li_{1.09}Co_{0.97}Mg_{0.02}Ti_{0.01}O_{1.95}F_{0.05}$ | $Li_{1.04}Ni_{0.80}Co_{0.10}Mn_{0.07}Zr_{0.01}Al_{0.02}O_{1.9}F_{0.1}$ | 70:30 |
| Example 28 | $Li_{1.05}Co_{0.97}Mg_{0.01}Zr_{0.01}Al_{0.01}O_{1.9}Cl_{0.1}$ | $Li_{1.07}Ni_{0.80}Co_{0.10}Mn_{0.07}Zr_{0.01}Ti_{0.01}Al_{0.01}O_{1.9}S_{0.1}$ | 70:30 |
| Example 29 | $Li_{1.08}Co_{0.97}Mg_{0.01}Zr_{0.01}Al_{0.01}O_{1.9}S_{0.1}$ | $Li_{1.02}Ni_{0.80}Co_{0.10}Mn_{0.06}Mg_{0.02}Zr_{0.015}Ti_{0.005}O_{1.9}S_{0.1}$ | 70:30 |
| Example 30 | $Li_{1.085}Co_{0.98}Zr_{0.01}Ti_{0.005}Al_{0.005}O_{1.9}Cl_{0.1}$ | $Li_{1.05}Ni_{0.80}Co_{0.10}Mn_{0.07}Mg_{0.01}Zr_{0.01}Al_{0.01}O_{1.9}Cl_{0.1}$ | 70:30 |
| Comparative Example 1 | $LiCoO_2$ | / | / |
| Comparative Example 2 | $Li_{1.01}Co_{0.98}Mg_{0.01}Ti_{0.005}Al_{0.005}O_2$ | / | / |

A test process for a lithium-ion battery is illustrated as follows.

(1) Cycle Performance Test of a Lithium-Ion Battery at Normal Temperature and High Voltage At 25° C., a lithium-ion battery is charged at a constant current of 1 C to a voltage of 4.35V, and further charged at a constant voltage of 4.35V to a current of 0.05 C, and then discharged at a constant current of 1 C to a voltage of 3.0V. This is a charge-discharge cycle process, a discharge capacity this time is a discharge capacity of the first cycle. The lithium-ion battery is subjected to 200 cycles of charge/discharge test according to the above method, and the discharge capacity of the 200th cycle is detected.

Capacity retention rate (%) of the lithium-ion battery after 200 cycles=(discharge capacity of the 200th cycle of the lithium-ion battery/discharge capacity of the first cycle of the lithium-ion battery)×100%.

(2) Cycle Performance Test of a Lithium-Ion Battery at High Temperature and High Voltage At 45° C., a lithium-ion battery is charged at a constant current of 1 C to a voltage of 4.35V, and further charged at a constant voltage of 4.35V to a current of 0.05 C, and then discharged at a constant current of 1 C to a voltage of 3.0V. This is a charge-discharge cycle process, a discharge capacity this time is a discharge capacity of the first cycle. The lithium-ion battery is subjected to 200 cycles of charge/discharge test according to the above method, and the discharge capacity of the 200th cycle is detected.

Capacity retention rate (%) of the lithium-ion battery after 200 cycles=(discharge capacity of the 200th cycle of the lithium-ion battery/discharge capacity of the first cycle of the lithium-ion battery)×100%.

(3) Storage Performance Test of a Lithium-Ion Battery at High Temperature

At 25° C., a lithium-ion battery is charged at a constant current of 0.5 C to a voltage of 4.35V, and further charged at a constant voltage of 4.35V to a current of 0.05 C, and at this time, a thickness of the lithium-ion battery is tested and recorded as $h_0$; afterwards, the lithium-ion battery is put into a thermostat at 85° C., stored for 24 h before taken out, a thickness of the lithium-ion battery is tested at this time and record as $h_1$.

Thickness expansion rate (%) of lithium-ion battery stored at 85° C. for 24 h=[($h_1-h_0$)/$h_0$]×100%.

TABLE 3

Performance test results of Examples 1-30 and Comparative Examples 1-2

| | Capacity retention rate (%) after 200 cycles at 25° C./4.35 V | Capacity retention rate (%) after 200 cycles at 45° C./4.35 V | Thickness expansion rate at 85° C./24 h |
|---|---|---|---|
| Example 1 | 85% | 78% | 38% |
| Example 2 | 93% | 87% | 12% |
| Example 3 | 98% | 94% | 4% |
| Example 4 | 96% | 91% | 4% |
| Example 5 | 92% | 86% | 3% |
| Example 6 | 84% | 77% | 2% |
| Example 7 | 74% | 64% | 1% |
| Example 8 | 97% | 94% | 2% |
| Example 9 | 98% | 95% | 2% |
| Example 10 | 97% | 94% | 3% |
| Example 11 | 97% | 95% | 3% |
| Example 12 | 98% | 96% | 2% |
| Example 13 | 97% | 95% | 3% |
| Example 14 | 95% | 93% | 4% |
| Example 15 | 94% | 92% | 5% |
| Example 16 | 97% | 95% | 3% |
| Example 17 | 98% | 96% | 2% |
| Example 18 | 97% | 94% | 3% |
| Example 19 | 97% | 95% | 3% |
| Example 20 | 96% | 94% | 3% |
| Example 21 | 98% | 96% | 2% |
| Example 22 | 97% | 95% | 3% |
| Example 23 | 96% | 94% | 4% |
| Example 24 | 98% | 95% | 3% |
| Example 25 | 97% | 95% | 3% |
| Example 26 | 98% | 96% | 3% |
| Example 27 | 98% | 96% | 2% |
| Example 28 | 99% | 97% | 2% |
| Example 29 | 99% | 96% | 2% |
| Example 30 | 99% | 97% | 1% |
| Comparative Example 1 | 84% | 77% | 44% |
| Comparative Example 2 | 90% | 83% | 15% |

It can be seen from the comparison between Examples 1-30 and Comparative Examples 1-2 that: the lithium-ion battery according to the present application has excellent cycle performance and storage performance under high temperature and high voltage conditions.

Compared with Comparative Example 1, Examples of the present application use a mixture of the lithium cobalt oxide material $Li_{x1}Co_{y1}M1_{1-y1}O_{2-a}Q1_a$ and the ternary material $Li_tNi_{m1}Co_{n1}M2_pM3_qO_{2-b}Q2_b$ as a positive active material, and use the additive A as an electrolytic additive. A certain amount of the ternary material is mixed into the lithium cobalt oxide material, the ternary material can be evenly distributed in gaps between particles of the lithium cobalt oxide material, and thus the lithium cobalt oxide material can be separated effectively, and at the same time, after mixing, the compaction density of the positive electrode sheet can also be increased, and the energy density of the lithium-ion battery can be increased; furthermore, high thermal stability of the ternary material can not only ensure its own structural stability, but also can effectively prevent heat transmission caused by the decomposition of local lithium cobalt oxide material, improving thermal stability of the entire positive electrode sheet. The additive A is a six-membered nitrogen heterocyclic compound with multiple nitrile groups and with low oxidation potential, and during formation of the battery, can form a stable complex layer on the surface of the positive active material, which can effectively passivate the surface of the positive active material, reduce activity of the surface of the positive active material, and isolate the direct contact between the electrolyte and the surface of the positive active material, so that surface side reactions are greatly reduced, and the lithium ions consumed in the side reactions are reduced correspondingly, in other words, the consumption rate of reversible lithium ions is greatly slowed down, and the actual effect finally revealed is that the cycle capacity retention rate of the lithium-ion battery is greatly increased; some surface side reactions can produce gas, the reduction of surface side reaction also means that the gas production in the battery is reduced, and the actual effect finally revealed is that the thickness expansion of the lithium-ion battery is significantly reduced at high temperature.

Compared with a linear nitrile compound used in Comparative Example 2, the six-membered nitrogen heterocyclic compound with multiple nitrile groups according to the present application has a special six-membered nitrogen heterocyclic structure, a distance between nitrile groups is closer to a distance between transition metals on the surface of the positive active material, which can maximize the complexation of nitrile groups, and make maximum quantity of nitrile groups perform the complexation. Therefore, the six-membered nitrogen heterocyclic compound with multiple nitrile groups according to the present application has a stronger covering effect on the transition metal on the surface of the positive active material, has a better passivation effect on the surface of the positive active material, and has a more outstanding improvement effect on the cycle performance and storage performance of the lithium-ion battery.

It can also be seen from Examples 1-7 that, with increase in the amount of the additive A (increased from 0.1% to 10%), under a condition that the end-of-charge voltage is maintained at 4.35V, the cycle capacity retention rate of the lithium-ion battery at 25° C. and 45° C. reaches the best, and then a downward trend occurs, and when stored at 85° C. for 24 h, the thickness expansion rate is kept decreasing. This is because, when the addition amount of the additive A is relatively large, firstly, the complex layer formed by the additive A adsorbed onto the surface of the positive active material is easy to be thicker and denser, which affects the diffusion and migration of lithium ions, and greatly increases impedance of the positive electrode; secondly, the additive A will consume lithium ions when forming the complex layer, resulting in a decrease of lithium ions available for recycling; finally, when the addition amount of the additive A is relatively high, the overall viscosity of the electrolyte will increase and the ionic conductivity will decrease, and finally, the cycle capacity retention rate of the lithium-ion battery at 25° C. and 45° C. reaches the best, and then a downward trend occurs. Therefore, the addition amount of the additive A is required to be appropriate, which is preferably 0.1%-10%, more preferably 0.1%-6%, further more preferably 0.1%-3.5%.

Examples 25-27 explore effects of $LiBF_4$ on the performance of the lithium-ion battery under a condition that the addition amount of the additive A is optimal. Compared with Example 3, Examples 25-28 have a smaller thickness expansion rate when stored at 85° C. for 24 h, this is because the B atom in $LiBF_4$ can stabilize the oxygen atom in the positive active material, and play a role in inhibiting release of oxygen from the positive active material, and therefore, the lithium-ion battery shows a better storage performance.

Examples 28-30 explore effects of VC, FEC and PS on the performance of the lithium-ion battery under a condition that the addition amount of the additive A is optimal. These additives help to form a surface film containing double bonds, fluorine atoms, and sulfonate groups on a surface of the positive or negative electrode. The surface film has good chemical, electrochemical, mechanical and thermal stability, can smoothly conduct lithium ions and meanwhile isolate the direct contact between the electrolyte and the surfaces of the positive and negative electrodes, and plays a role in inhibiting oxidation and reduction side reactions of the surfaces of the positive and negative electrodes. Therefore, after addition, they help to further improve the cycle performance and the storage performance of the lithium-ion battery.

Based on the disclosure and teaching in the above description, those skilled in the art can further make appropriate variations and modifications to the above embodiments. Therefore, the present application is not limited to the specific embodiments disclosed and described above, and some modifications and variations to the present application shall also fall within the protection scope of claims of the present application. Furthermore, although some specific terms are used in the description, these terms are used only for convenience of illustration and do not constitute any limitation on the present application.

What is claimed is:

1. A lithium-ion battery, comprising an electrode assembly and an electrolyte, the electrode assembly comprising a positive electrode sheet, a negative electrode sheet, and a separator;

wherein a positive active material of the positive electrode sheet comprises both $Li_{x1}Co_{y1}M1_{1-y1}O_{2-a}Q1_a$ and $Li_1Ni_{m1}Co_{n1}M2_pM3_qO_{2-b}Q2_b$, a mass ratio of $Li_{x1}Co_{y1}M1_{1-y1}O_{2-a}Q1_a$ and $Li_1Ni_{m1}Co_{n1}M2_pM3_qO_{2-b}Q2_b$ is 1:1-9:1;

wherein $0.5 \leq x1 \leq 1.2$, $0.8 \leq y1 < 1.0$, $0 \leq a \leq 0.1$, M1 is selected from the group consisting of Al, Ti, Zr, Y, and Mg, and Q1 is selected from the group consisting of F, Cl, and S; $0.5 \leq 1 \leq 1.2$, $0.33 \leq m1 \leq 0.85$, $0.1 \leq n1 \leq 0.33$, $0.1 \leq p \leq 0.33$, $0 \leq q \leq 0.1$, and $m1+n1+p+q=1$, $0 \leq b \leq 0.1$, M2 is selected from the group consisting of Mn and Al, M3 is selected from the group consisting of Zr, Zn, Cu, Cr, Mg, Fe, V, Ti, Y, and Nb, and Q2 is selected from one or more of F, Cl, and S;

the electrolyte comprises an additive A, the additive A is selected from the group consisting of compounds represented by Formula I-1, Formula I-2, and Formula I-3;

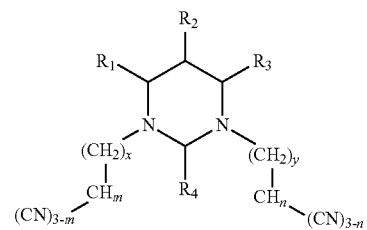

Formula I-1

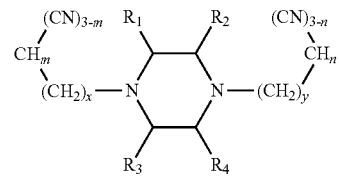

Formula I-2

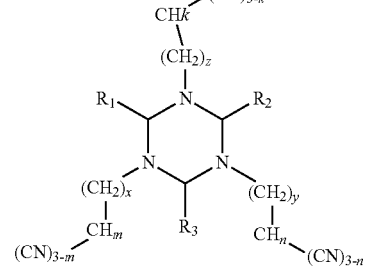

Formula I-3 in the Formula I-1, Formula I-2 and Formula I-3: $R_1$, $R_2$, $R_3$ and $R_4$ each are independently selected from the group consisting of a hydrogen atom, a halogen atom, a substituted or unsubstituted $C_1$-$C_{12}$ alkyl group, a substituted or unsubstituted $C_1$-$C_{12}$ alkoxyl group, a substituted or unsubstituted $C_1$-$C_{12}$ amido group, a substituted or unsubstituted $C_2$-$C_{12}$ alkenyl group, a substituted or unsubstituted $C_2$-$C_{12}$ alkynyl group, a substituted or unsubstituted $C_6$-$C_{26}$ aryl group, and a substituted or unsubstituted $C_2$-$C_{12}$ heterocyclyl group, wherein a substituent is selected from the group consisting of a halogen atom, a nitrile group, a $C_1$-$C_6$ alkyl group, a $C_2$-$C_6$ alkenyl group, and $C_1$-$C_6$ alkoxyl group; x, y and z each are independently selected from an integer of 0-8; m, n and k each are independently selected from an integer of 0-2;

wherein based on a total mass of the electrolyte, a mass percentage content of the additive A is 0.1%-3.5%.

2. The lithium-ion battery according to claim 1, wherein in the Formula I-1, Formula I-2 and Formula I-3: $R_1$, $R_2$, $R_3$ and $R_4$ each are independently selected from the group consisting of hydrogen atom, a halogen atom, a substituted or unsubstituted $C_1$-$C_3$ linear or branched alkyl group, a substituted or unsubstituted $C_5$-$C_7$ cyclic alkyl group, a substituted or unsubstituted $C_1$-$C_3$ alkoxyl group, a substituted or unsubstituted $C_1$-$C_3$ amido group, a substituted or unsubstituted $C_2$-$C_3$ alkenyl group, a substituted or unsubstituted $C_2$-$C_3$ alkynyl group, a substituted or unsubstituted $C_6$-$C_8$ aryl group, and a substituted or unsubstituted $C_2$-$C_7$ heterocyclyl group, wherein the substituent is selected from halogen atoms;

x, y and z each are independently selected from 0, 1 or 2; and m, n and k each are independently selected from 1 or 2.

3. The lithium-ion battery according to claim 1, wherein in the Formula I-1, $R_1$, $R_3$ and $R_4$ are the same group;

in the Formula I-2, at least three of $R_1$, $R_2$, $R_3$ and $R_4$ are the same group; and in the Formula I-3, at least two of $R_1$, $R_2$ and $R_3$ are the same group.

4. The lithium-ion battery according to claim 3, wherein in the Formula I-1, $R_1$, $R_3$ and $R_4$ are hydrogen atoms;

in the Formula I-2, at least three of $R_1$, $R_2$, $R_3$ and $R_4$ are hydrogen atoms; and in the Formula I-3, at least two of $R_1$, $R_2$ and $R_3$ are hydrogen atoms.

5. The lithium-ion battery according to claim 1, wherein the additive A is selected from one or more of the following compounds:

Formula I-1 (a)

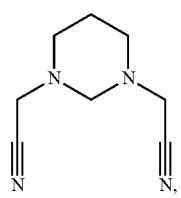

Formula I-1 (b)

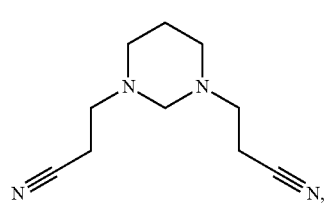

Formula I-1 (c)

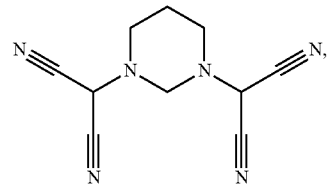

Formula I-1 (d)

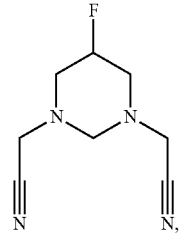

Formula I-1 (e)

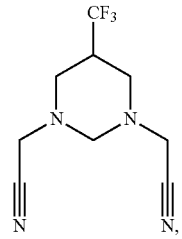

Formula I-1 (f)

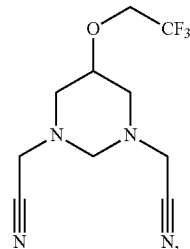

Formula I-1 (g)

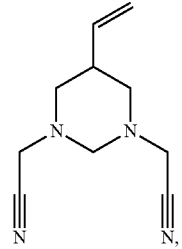

Formula I-1 (h)

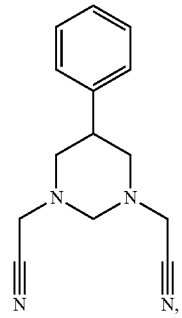

-continued
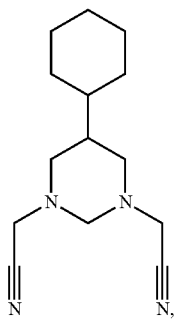
Formula I-1 (i)
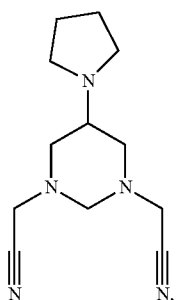
Formula I-1 (j)
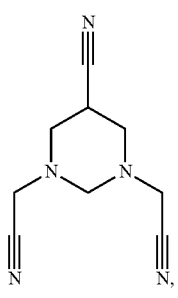
Formula I-1 (k)
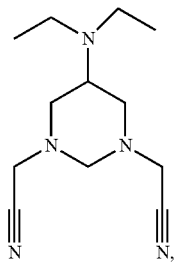
Formula I-1 (l)
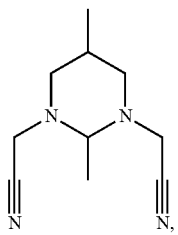
Formula I-1 (m)
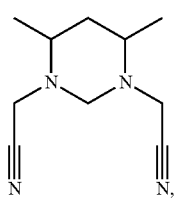
Formula I-1 (n)
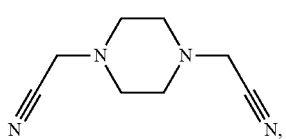
Formula I-2 (a)
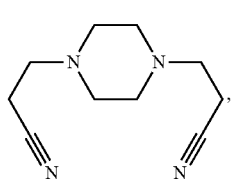
Formula I-2 (b)
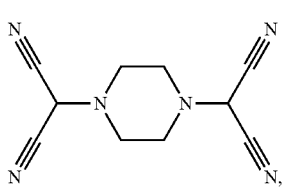
Formula I-2 (c)
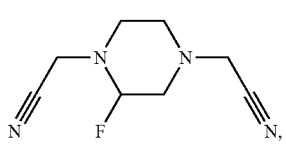
Formula I-2 (d)
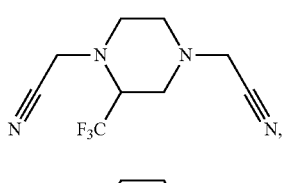
Formula I-2 (e)
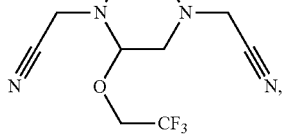
Formula I-2 (f)
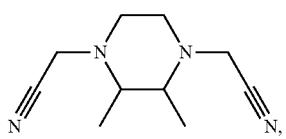
Formula I-2 (g)
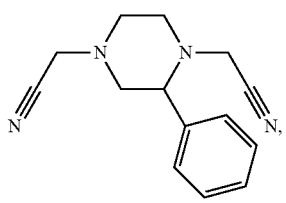
Formula I-2 (h)
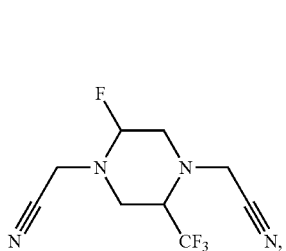
Formula I-2 (i)
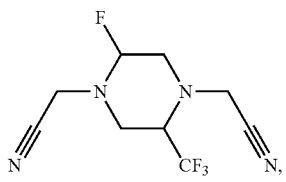

Formula I-3 (a)
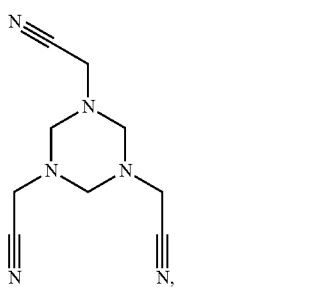

Formula I-3 (b)
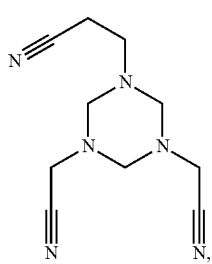

Formula I-3 (c)
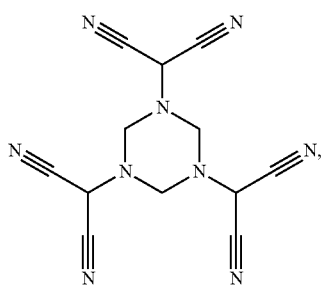

Formula I-3 (d)
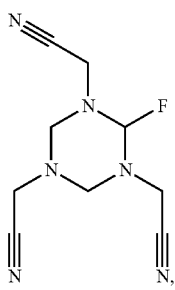

Formula I-3 (e)
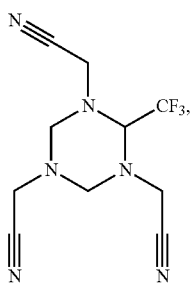

Formula I-3 (f)
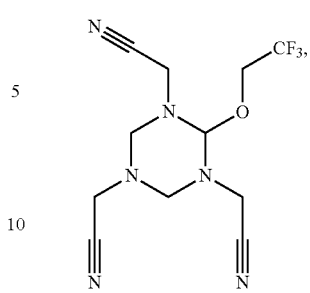

Formula I-3 (g)
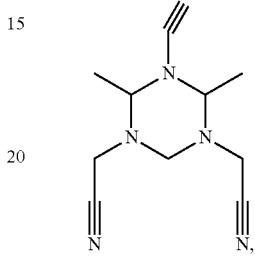

Formula I-3 (h)
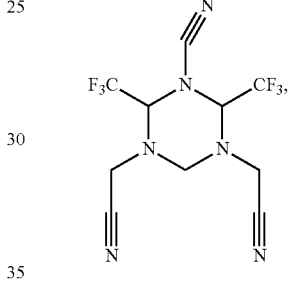

Formula I-3 (i)
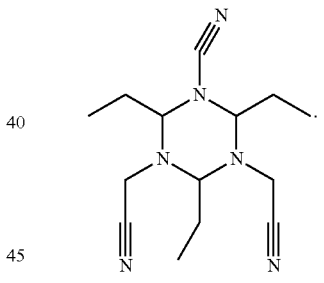

6. The lithium-ion battery according to claim 1, wherein the electrolyte further comprises an additive B, and the additive B is $LiBF_4$; and, based on the total mass of the electrolyte, a mass percentage content of the additive B is 0.1%-5%.

7. The lithium-ion battery according to claim 1, wherein the electrolyte further comprises an additive C, the additive C is selected from the group consisting of vinylene carbonate, fluoroethylene carbonate, and 1,3-propane sultone; and, based on the total mass of the electrolyte, a mass percentage content of the additive C is 0.1%-5%.

8. The lithium-ion battery according to claim 1, wherein the lithium-ion battery is a hard-shell lithium-ion battery or a soft-package lithium-ion battery.

9. The lithium-ion battery according to claim 1, wherein an end-of-charge voltage of the lithium-ion battery is 4.35V.

10. An apparatus, comprising the lithium-ion battery according to claim 1.

* * * * *